US007601357B2

(12) United States Patent
Kolattukudy et al.

(10) Patent No.: US 7,601,357 B2
(45) Date of Patent: Oct. 13, 2009

(54) TARGETING OF LONG CHAIN TRIACYLGLYCEROL HYDROLASE GENE FOR TUBERCULOSIS TREATMENT

(75) Inventors: Pappachan E. Kolattukudy, Orlando, FL (US); Chirajyoti Deb, Oviedo, FL (US); Jaiyanth Daniel, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 11/561,460

(22) Filed: Nov. 20, 2006

(65) Prior Publication Data

US 2007/0161562 A1 Jul. 12, 2007

Related U.S. Application Data

(60) Provisional application No. 60/748,284, filed on Dec. 7, 2005.

(51) Int. Cl.
*A61K 39/04* (2006.01)
*A61K 39/00* (2006.01)
*C07H 21/04* (2006.01)

(52) U.S. Cl. ...................... 424/248.1; 424/9.1; 424/9.2; 424/130.1; 424/139.1; 424/150.1; 424/184.1; 424/185.1; 424/190.1; 424/234.1; 530/300; 530/350; 536/23.1; 536/23.7

(58) Field of Classification Search .................. 424/9.1, 424/9.2, 130.1, 139.1, 150.1, 184.1, 185.1, 424/190.1, 234.1, 248.1; 530/300, 350; 536/23.1, 536/23.7
See application file for complete search history.

(56) References Cited

OTHER PUBLICATIONS

Deb, C., et al. A novel lipase belonging to the hormone-sensitive lipase family induced under starvation to utilize stored triacylglycerol in Mycobacterium tuberculosis. J. biol. Chem., vol. 281, No. 7, pp. 3866-3875, 2006.*

* cited by examiner

*Primary Examiner*—Rodney P. Swartz
(74) *Attorney, Agent, or Firm*—Timothy H. Van Dyke; Beusse Wolter Sanks Mora & Maire

(57) ABSTRACT

Disclosed herein are novel methods for screening for compounds useful in treating or preventing tuberculosis. In exemplary embodiments, screening methods are based on the implementation or manipulation of triacylglycerol hydrolase like polypeptides or polynucleotides encoding the same. The methods are useful in identifying agents active against TB infection.

18 Claims, 8 Drawing Sheets

```
LipY (Rv3097c)      SEQ ID NO. 69            233 EYVVAIHGGAFILPPSIF--HWLNYSVTAYQTGATVQVPIYPLVQEGGTAGTVVPAMAGL 287
A. fulgidus         SEQ ID NO. 70             80 PVLVYYHGGGFVICSIES--HDALCRRIARLSNSTVVSVDYRLAPEHKFPAAVYDCYDAT 137
Acinetobacter esterase SEQ ID NO.71           68 PLIVFYHGGGFVVGGLDS--HDEFCRLMAVHAHAQVLSVEYPLAPEASPQQIIQVCEDAL 125
H. sapiens HSL      SEQ  ID NO. 72           645 SLIVHFHGGGFVAQTSRS--HEPYLKSWAQELGAPIISIDYSLAPEAPFPRALEECFFAY 702
Pseudomonas B11-1 lipase SEQ. ID NO.73        74 PLLVFFHGGGFVMGNLDT--HDNLCRSLASQTEAVVVSVAYRLAPENHFPAAPLDCYAAT 132
B. subtilis brefeldinA esterase              119 PGLVYTHGGGMTILTTDNRVHRRWCTDLAAAGSVVVMVDFRNAWTAEGHHPFPSGVEDCL 178
        SEQ ID NO. 74
CDC1551 esterase SEQ ID NO. 75               125 RAVLYLHGGAFLTCGANS--HGRLVELLSKFADSPVLVVDYRLIPKHSIGMALDDCHDGY 180
CDC1551 PE-family SEQ ID NO. 76              233 EYVVAIHGGAFILPPSIF--HWLNYSVTAYQTGATVQVPIYPLVQEGGTAGTVVPAMAGL 288
R. solanacearum     SEQ ID NO. 77             77 PVVFYLHGGGYLFCSPRI--HRSITIGLAVHARARVFALDYRLAPEHPFPAAVLDALAGY 132
S. aureus 2323      SEQ ID NO. 78            100 RVVLYAHGGAWFQDPLKI--HFEFIDELAETLNAKVIMPVYPKIPHQDYQATYVLFEKLY 155
                                                 ▼
LipY (Rv3097c) SEQ ID NO. 69(cont.)          301 SNVSVVGDSAGGNLALAAAQYMVSQGNPVPSSMVLLSPWLDVGTWQISQAWAGNLAVN 358
A. fulgidus SEQ ID NO. 70 (cont)             152 SKIFVGGDSAGGNLAAAVSIMARDSGEDFIKHQILIYPVVNFVAPTPSLLEFGEGLWI 209
Acinetobacter esterase SEQ ID NO. 71 (cont.) 140 NRIAVAGDSAGGNIAAVVAQRSAQSAYAPNA-QFLIYPALDFKSRHPSFFAYKDGLVL 196
H. sapiens HSL SEQ ID NO. 72 (cont)          717 ERICLAGDSAGGNLCFTVALRAAAYGVRVPDGIMAAYPATMLQPAASPSRLLSLMDPL 774
Pseudomonas B11-1 lipase SEQ ID No. 73(cont) 147 RRLALAGDSAGGNLALAVSRLAAQRQGPKISYQCLFYPVTDARCDSQSYEEFAEGYFL 204
B. subtilis brefeldinA esterase SEQ ID 74 (cont) 194 SGVVVQGESGGGNLAIATTLLAKRRGRLDAIDGVYASIPYISGGYAWDHERRLTELPS 251
CDC1551 esterase SEQ ID NO. 75 (cont)        193 EQIVLAGDSAGGYLALALAQRLQEVGEEPAALVAISPLLQLAKEHKQAHPNIKTDAMF 250
CDC1551 PE-family   SEQ ID NO. 76 (cont)     303 SNVSVVGDSAGGNLALAAAQYMVSQGNPVPSSMVLLSPWLDVGTWQISQAWAGNLAVN 358
R. solanacearum SEQ ID NO. 77 (cont)         146 SRIVVAGDSAGGGLSLALLVALRDAGDPLPAGAILYSPWTDLAATGASLVENDASDVM 201
S. aureus 2323 SEQ ID NO. 78 (cont)          168 KQIVVMGDSAGGQIALSFAQLLKEKHIVQPGHIVLISPVLDATMQHPEIPDYLKKDPM 225
                                                  ▼                        ▼
LipY (Rv3097c) SEQ ID NO. 69 (cont)          372 LPPTYVYSGSLDPLAQQAVVLEHTAVVQGAPFSFVLAPWQIHDWILLTP-----WGLLSWPQINQQL  433
A. fulgidus SEQ ID NO. 70 (cont)             244 LPPALIITAEYDPLRDEGEVFGQMLRRAGVEASIVRYRGVLHGF--INYYPVLKAARDAINQIAALL  308
Acinetobacter esterase SEQ.ID NO.71(cont)    231 LAPAFVVTAGHDVLHDEAEIYAHKLRQNQVTVKYVEYLEQTHGF--ISMTFVSRRAKKISIELCKNF  295
H. sapiens HSL SEQ ID NO. 72 (cont)          983 LPPVHIVACALDPMLDDSVMLARRLRNLGQPVTLRVVEDLPHGFLTLAALCRETRQAAELCVERIRL 1049
Pseudomonas B11-1 lipase SEQ ID NO. 73 (cont) 239 LPPTTLITAEFDPLRDEGEAFALRLQQAGVSVRVQRCEGMIHGFISMAPFVERAAHALSDAAADLRR  305
B. subtilis brefeldinA esterase              297 LPPFVVAVNELDPLRDEGIAFARRLARAGVDVAARVNIGLVHGADVIFRHWLPAALESTVRDVAGFA  363
        SEQ ID. 74 (cont)
CDC1551 esterase  SEQ ID NO. 75 (cont)       289 LPRTLIHVSGSEVLLHDAQLAAAKLAAAGVPAEVRVWPGQVHDFQVAASM--LPEAIRSLRQIGEYI  352
CDC1551 PE-family  SEQ ID NO. 76 (cont)      372 LPPTYVYSGSLDPLAQQAVVLEHTAVVQGAPFSFVLAPWQIHDWILLTP-----WGLLSWLQINQQL  433
R. solanacearum  SEQ ID NO. 77 (cont)        237 LPPLHCYVGTSEVLRDDTERMAERARAAGVSVSVELERRLPHVWPIFYPF--LPEARKALRQSGDAV  301
S. aureus 2323 SEQ ID NO. 78 (cont)          259 LGRITLTVGTKEVLYPDALNLSQLLSAKGIEHDFIPEYYQFHIYPVFPI----PERRRFLYQVKNII  321
```

TARGETING OF LONG CHAIN TRIACYLGLYCEROL HYDROLASE GENE FOR TUBERCULOSIS TREATMENT

CROSS-REFERENCE TO RELATED APPLICATIONS

This application is related to U.S. Provisional Patent No. 60/748,284, filed Dec. 7, 2005, which is incorporated herein by reference. Priority is claimed under 35 USC § 119.

GOVERNMENT SUPPORT

This invention was made through support from the NIH, Grant Nos. AI46582 and AI35272. The government may have certain rights in this invention.

BACKGROUND

Tuberculosis (TB) has been a major health problem for most of recorded history and *Mycobacterium tuberculosis* remains one of the world's most significant pathogens. Responsible for millions of new cases of tuberculosis annually (see e.g. Pablo-Mendez et al., (1998) New Engl. J. Med. 338, 1641-1649), it is the leading cause of death from a single infectious agent. While the incidence of the disease declined in parallel with advancing standards of living since at least the mid-nineteenth century, in spite of the efforts of numerous health organizations worldwide, the eradication of tuberculosis has never been achieved, nor is imminent.

TB is acquired by the respiratory route; actively infected individuals spread this infection efficiently by coughing or sneezing "droplet nuclei" which contain viable bacilli. Overcrowded living conditions and shared air spaces are especially conducive to the spread of TB, underlying the increase in instances that have been observed in the U.S. in prison inmates and among the homeless in larger cities.

Medical experts estimate that about 10 million Americans are infected with TB bacteria, and about 10 percent of these people will develop active TB in their lifetime. However, TB is an increasing worldwide problem, especially in Africa. It is estimated that, worldwide, about one billion people will become newly infected, over 150 million people will contract active TB, and 36 million people will die between now and 2020 unless TB control is improved.

The emergence of multi-drug resistant strains of *Mycobacterium tuberculosis* poses serious threats to the control of this disease due to the complex nature of second-line drug treatment (WHO Report. (2004) *WHO/HTM/TB/*2004.343). Upon infection the bacterium goes through an initial replicative phase inside the alveolar macrophages after which it enters a non-replicative, drug-resistant state of dormancy. This state of dormancy is probably induced by the environmental stress exerted upon the pathogen by the host's immune response. The bacterium is able to survive in this dormant state for decades until the host's immune system is weakened when it reactivates and causes the infectious disease (Dannenberg, Jr., A. M., and Rook G. A. W. (1994) In *Tuberculosis: Pathogenesis, Protection and Control*, Bloom, B. R., (Ed.) American Society of Microbiology, Washington D.C.). The current anti-mycobacterial drugs are able to kill only the actively replicating mycobacteria and do not clear the latent bacteria from the host (Honer zu Bentrup, K., and Russell D. G. (2001) *Trends Microbiol.* 9, 597-605). Thus latency is a major problem in TB control. One-third of the world population is infected with the latent microorganism and nearly two million deaths occur annually (Dye, C., Scheele, S., Dolin, P., Pathania, V., and Raviglione M. C. (1999) *JAMA.* 282, 677-686, WHO Report. (2005) *WHO/HTM/TB/*2005). Individuals carrying a latent infection are estimated to harbor a 2-23% lifetime risk of reactivation (Zahrt, T. C. (2003). *Microbes Infect.* 5, 159-167).

If an individual has TB disease, i.e., has active TB, the individual typically is administered a combination of several drugs. It is very important, however, that the individual continue a correct treatment regimen for the full length of the treatment. If the drugs are taken incorrectly, or stopped, the individual can suffer a relapse and will be able to infect others with TB.

When an individual becomes sick with TB a second time, the TB infection may be more difficult to treat because the TB bacteria have become drug resistant, i.e., TB bacteria in the body are unaffected by some drugs used to treat TB. Multi-drug-resistant tuberculosis (MDR TB) is a very dangerous form of tuberculosis. In particular, some TB bacteria become resistant to the effects of various anti-TB drugs, and these resistant TB bacteria then can cause TB disease. Like regular TB, MDR TB can be spread to others.

To avoid drug resistance in the treatment of TB, a four-drug regimen, i.e., isoniazid, rifampin, pyrazinamide, and streptomycin, is administered to TB patients. Aminoglycosides, such as streptomycin, are important anti-TB agents, but their utility is restricted by the requirement of parenteral administration, which is inconvenient and leads to poor patient compliance. It is theorized that poor patient compliance also can lead to the development of drug resistance, and it appears that the frequency of streptomycin resistance among anti-TB drugs is surpassed only by isoniazid.

In view of the above, an urgent need exists for new anti-TB agents useful in an effective treatment regimen for both the active and latent TB, and that effectively treat TB caused by multidrug resistant (MDR) strains of bacteria. Therefore, it would be advantageous to provide compounds and compositions for administration to an individual in the treatment of tuberculosis.

BRIEF DESCRIPTION OF THE DRAWINGS

FIG. 8: Structure-based alignment of the conserved domains of LIPY with lipases from the HSL family. The multiple sequence alignment produced by Cn3D was used to align other members of the HSL family with LIPY using ClustalW and the output was manually adjusted for optimal alignment. The sequences selected for alignment with LIPY (SEQ ID NO: 69) are *A. fulgidus* carboxylesterase (GI 17943077; SEQ ID NO: 70), *Acinetobacter* esterase (GI 34559428; SEQ ID NO: 71)), Human HSL (GI 21328445; SEQ ID NO: 72), *Pseudomonas* B11-1 lipase (GI 2853612; SEQ ID NO: 73), *B. subtilis* brefeldin A esterase (GI 414722; SEQ ID NO: 74), *M. tuberculosis* CDC1551 esterase (GI 15840511; SEQ ID NO: 75), *M. tuberculosis* CDC1551 PE family protein (GI 15842668; SEQ ID NO: 76), *R. solanacearum* putative esterase/lipase (GI 17545158; SEQ ID NO: 77), and *S. aureus* hypothetical protein (GI 15928114; SEQ ID NO: 78). Black shading indicates residues conserved in seven or more aligned sequences and shades of gray are used to indicate residues conserved in a few sequences. ▼, amino acids belonging to the catalytic triad. The ClustalW program was accessed from the European Bioinformatics Institute website www.ebi.ac.uk.

DETAILED DESCRIPTION

Figure 1:
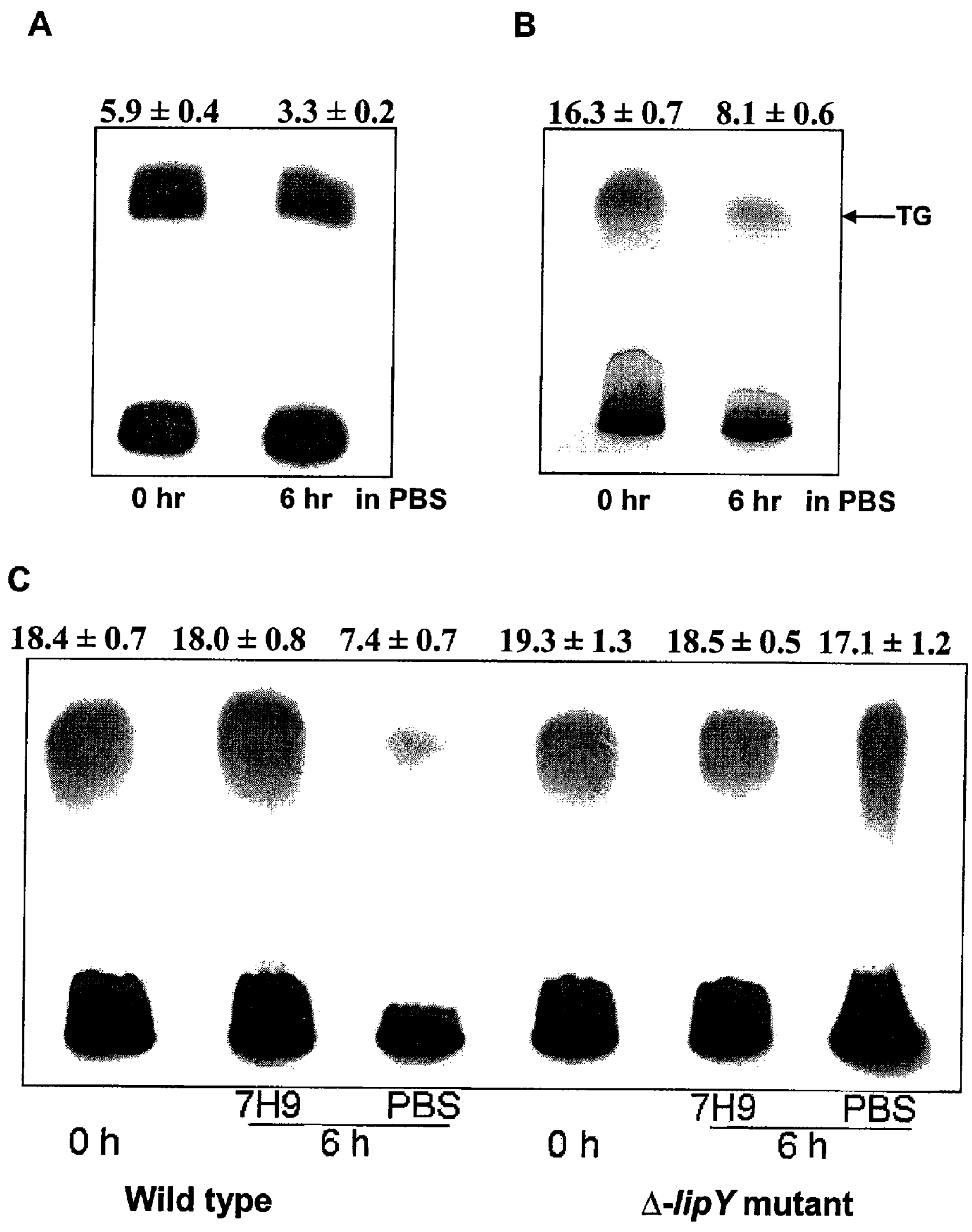
FIG. 1: Triacylglycerol (TG) utilization by *M. tuberculosis* wild type and lipY mutant cells under nutrient starvation condition. (A) Autoradiogram and (B) dichromate/sulfuric acid chaffing of lipids showing utilization of TG by wild type *M. tuberculosis* in PBS medium. After 12 days of hypoxic growth, cells were incubated with 1 μCi of $^{14}$C-oleic acid for 1 hr and the cells were washed with PBS prior to 6 hr incubation in same media. (C) Dichromate/sulfuric acid chaffing of lipids showing utilization of TG accumulated during 12 days of hypoxic growth of *M. tuberculosis* (wild type) and lipY mutant cells at 0 h and by 6 h incubation in PBS and nutrient rich (7H9) media. Lipids were separated on Silica gel TLC using n-hexane:diethyl ether (9:1, v/v) as developing solvent. In panel A, autoradiogram is shown from a typical experiment and the incorporation values of $^{14}$C into TG is shown as a percentage of the total $^{14}$C administered. In panel B and C, charred TLC chromatograms are shown from a typical experiment and the intensity of the TG band was determined in arbitrary units by the AlphaImager 2200 Gel Doc system. On top of each panel, the values are given as SEM of three independent measurements.

The ability of *Mycobacterium tuberculosis* to go into a latent/dormant state and survive under such conditions for decades make TB control extremely difficult. Developing drugs targeted at the ability of the pathogen to survive under such latent conditions for long periods is one way to fight against latent TB. The invention is based, in part, on the inventors discovery of a novel TB gene (Rb3097c) encoding an enzyme required for *Mycobacterium tuberculosis* to process energy in order to enter, survive, or exit the dormancy (or latent) period. The gene sequence is provided as SEQ ID NO:1. The inventors believe that triacylglycerol (TG) could be used as an energy source by *M. tuberculosis* during the dormancy period, thus its synthesis or its metabolism could be an ideal drug target against latent TB.

Accordingly, the inventors have screened putative lipase/esterase gene products from *M. tuberculosis* for long-chain TG hydrolase activity and have discovered that the Rv3097c gene product, is active as a true lipase. LIPY (PE-PGRS63), which is a member of PE-PGRS protein family, is a lipase belonging to the hormone-sensitive lipase (HSL) family and hydrolyzes long-chain TG with high specific activity. The inventors have also found that lipY is upregulated to a much higher level than the transcripts of other lipase/esterase-like genes when mycobacteria that accumulated TG during an in vitro dormancy-like state were subjected to TG utilizing conditions indicating that this lipase plays a role in the utilization of TG for survival through dormancy. The inventors disclose herein that the ability to hydrolyze stored TG was drastically diminished in a lipY disrupted mutant (Δ-lipY).

Thus, one embodiment of the subject invention pertains to a method of screening for therapeutic agents useful in the treatment of *Mycobacterium tuberculosis* infection in a mammal comprising the steps of i) contacting a test compound with a *M. tuberculosis* TG hydrolase (MTTGH) polypeptide, ii) detecting binding of said test compound to said MTTGH polypeptide.

Another embodiment the subject invention is directed to a method of screening for therapeutic agents useful in the treatment of *Mycobacterium tuberculosis* infection in a mammal comprising the steps of i) determining the activity of a MTTGH polypeptide at a certain concentration of a test compound or in the absence of said test compound, ii) determining the activity of said polypeptide at a different concentration of said test compound. These and other embodiments will be described in further detail herein.

1. Screening Methods

The invention provides assays for screening test compounds which bind to or modulate the activity of an MTTGH polypeptide or bind to and inhibit or affect expression of an MTTGH polynucleotide. A test compound preferably binds to an MTTGH polypeptide. More preferably, a test compound decreases or increases MTTGH activity by at least about 10, preferably about 50, more preferably about 75, 90, or 100% relative to the absence of the test compound.

1.1. Test Compounds

Test compounds relate to agents that potentially have therapeutic activity, i.e., bind to or modulate the activity of an MTTGH polypeptide or bind to or affect expression of an MTTGH polynucleotide. Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994).

1.2. High Throughput Screening

Test compounds can be screened for the ability to bind to and inhibit MTTGH polypeptides or polynucleotides or to affect MTTGH activity or MTTGH gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 μl. In addition to the plates, many instruments, materials, pipettors, robotics, plate washers, and plate readers are commercially available to fit the 96-well format.

Alternatively, "free format assays," or assays that have no physical barrier between samples, can be used.

1.3. Binding Assays

For binding assays, the test compound is preferably, but not necessarily, a small molecule which binds to and occupies, for example, the active site of the MTTGH polypeptide, such that normal biological activity is prevented. Examples of such small molecules include, but are not limited to, small peptides or peptide-like molecules.

In binding assays, either the test compound or the MTTGH polypeptide can comprise a detectable label, such as a fluorescent, radioisotopic, chemiluminescent, or enzymatic label, such as horseradish peroxidase, alkaline phosphatase, or luciferase. Detection of a test compound which is bound to the MTTGH polypeptide can then be accomplished, for example, by direct counting of radioemmission, by scintillation counting, or by determining conversion of an appropriate substrate to a detectable product.

Those skilled in the art equipped with teachings herein will appreciate that there are multiple conventional methods of detecting binding of a test compound. For example, binding of a test compound to a MTTGH polypeptide can be determined without labeling either of the interactants. A microphysiometer can be used to detect binding of a test compound with an MTTGH polypeptide. A microphysiometer (e.g., CYTOSENSOR™) is an analytical instrument that measures the rate at which a cell acidifies its environment using a light-addressable potentiometric sensor (LAPS). Changes in this acidification rate can be used as an indicator of the interaction between a test compound and an MTTGH polypeptide (McConnell et al., Science 257, 19061912, 1992).

In another alternative example, determining the ability of a test compound to bind to an MTTGH polypeptide can be accomplished using a technology such as real-time Bimolecular Interaction Analysis (BIA) (Sjolander & Urbaniczky, Anal Chem. 63, 23382345, 1991, and Szabo et al., Curr. Opin. Struct. Biol. 5, 699705, 1995). BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, an MTTGH polypeptide can be used as a "bait protein" in a two-hybrid assay or three-hybrid assay (see, e.g., U.S. Pat. No. 5,283,317; Zervos et al., Cell 72, 223232, 1993; Madura et al., J. Biol. Chem. 268, 1204612054, 1993; Bartel et al., BioTechniques 14, 920924, 1993; Iwabuchi et al., Oncogene 8, 16931696, 1993; and Brent WO94/10300), to identify other proteins which bind to or interact with the MTTGH polypeptide and modulate its activity.

In many screening embodiments, it may be desirable to immobilize either the MTTGH polypeptide (or polynucleotide) or the test compound to facilitate separation of bound from unbound forms of one or both of the interactants, as well as to accommodate automation of the assay. Thus, either the MTTGH polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the MTTGH polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a MTTGH polypeptide (or polynucleotide) can be accomplished in any vessel suitable for containing the reactants. Examples of such vessels include microtiter plates, test tubes, and microcentrifuge tubes.

In a specific embodiment, the MTTGH polypeptide may be a fusion protein comprising a domain that allows the MTTGH polypeptide to be bound to a solid support. For example, glutathione S-transferase fusion proteins can be adsorbed onto glutathione sepharose beads (Sigma Chemical, St. Louis, Mo.) or glutathione derivatized microtiter plates, which are then combined with the test compound or the test compound and the nonadsorbed MTTGH polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a MTTGH polypeptide (or polynucleotide) or a test compound can be immobilized utilizing conjugation of biotin and streptavidin. Biotinylated MTTGH polypeptides (or polynucleotides) or test compounds can be prepared from biotinNHS(Nhydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a MTTGH polypeptide, polynucleotide, or a test compound, but which do not interfere with a desired binding site, such as the active site of the MTTGH polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the MTTGH polypeptide or test compound, enzyme-linked assays which rely on detecting an activity of the MTTGH polypeptide, and SDS gel electrophoresis under non-reducing conditions.

Screening for test compounds which bind to a MTTGH polypeptide or polynucleotide also can be carried out in an intact cell. Any cell which comprises a MTTGH polypeptide or polynucleotide can be used in a cell-based assay system. A MTTGH polynucleotide can be naturally occurring in the cell or can be introduced using techniques such as those described above. Binding of the test compound to a MTTGH polypeptide or polynucleotide is determined as described above.

1.4. Enzyme Assays

Test compounds can be tested for the ability to increase or decrease the TGS activity of a MTTGH polypeptide. TGS activity can be measured, for example, by adapting techniques such as that described in U.S. Pat. No. 4,529,693 (see Example 2). Enzyme assays can be carried out after contacting either a purified MTTGH polypeptide, a cell membrane preparation, or an intact cell with a test compound. A test compound which decreases TGS activity of a MTTGH polypeptide by at least about 10, preferably about 50, more preferably about 75, 90, or 100% is identified as a potential therapeutic agent for decreasing MTTGH activity. A test compound which increases TGS MTTGH polypeptide by at least about 10, preferably about 50, more preferably about 75, 90, or 100% is identified as a potential therapeutic agent for increasing TGS activity.

1.5. Gene Expression

In another embodiment, test compounds which increase or decrease MTTGH gene expression are identified. An MTTGH polynucleotide is contacted with a test compound, and the expression of an RNA or polypeptide product of the MTTGH polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of MTTGH mRNA or polypeptide expression in the cells can be determined by methods well known in the art for detecting mRNA or polypeptide. Either qualitative or quantitative methods can be used. The presence of polypeptide products of an MTTGH polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a MTTGH polypeptide.

Such screening can be carried out either in a cell-free assay system or in an intact cell. Any cell which expresses a MTTGH polynucleotide can be used in a cell-based assay system. The MTTGH polynucleotide can be naturally occurring in the cell or can be introduced using techniques such as those described above. Either a primary culture or an established cell line, such as CHO or human embryonic kidney 293 cells, can be used.

2. Pharmaceutical Compositions

The invention also pertains to pharmaceutical compositions comprising one or more therapeutic agents that are identified by screening methods that utilize MTTGH polypeptides and/or polynucleotides. Therapeutic agent(s) can be administered to a patient to achieve a therapeutic effect, i.e. useful in treatment of TB. Pharmaceutical compositions of the invention can comprise, for example, therapeutic agents identified by a screening method embodiment described herein, which are identified by their ability to bind to or affect activity of MTTGH polypeptides, or bind to and/or affect expression MTTGH polynucleotides. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones. In addition to the active ingredients, these pharmaceutical compositions can contain suitable pharmaceutically acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

This invention further pertains to the use of novel agents identified by the screening assays described above. Accordingly, it is within the scope of this invention to use a therapeutic agent identified as described herein in an appropriate animal model. For example, an agent identified as described herein (for example, but not limited to, a modulating agent, an antisense nucleic acid molecule, a specific antibody, ribozyme, or a MTTGH polypeptide binding molecule) can be used in an animal model to determine the efficacy, toxicity, or side effects of treatment with such an agent. Furthermore, this invention pertains to uses of novel agents identified by the above described screening assays for treatments as described herein.

Those skilled in the art will appreciate that numerous delivery mechanisms are available for delivering a therapeutic agent to an area of need. By way of example, the agent may be delivered using a liposome as the delivery vehicle. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. A liposome useful in the present invention comprises a lipid composition that is capable of fusing with the plasma membrane of the targeted cell to deliver its contents to the cell. Preferably, the transfection efficiency of a liposome is about 0.5 μg of DNA per 16 nmole of liposome delivered to about $10^6$ cells, more preferably about 1.0 μg of DNA per 16 nmole of liposome delivered to about $10^6$ cells, and even more preferably about 2.0 μg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods which are standard in the art (see, for example, U.S. Pat. No. 5,705,151). Preferably, from about 0.1 μg to about 10 μg of polynucleotide is combined with about 8 nmol of liposomes, more preferably from about 0.5 μg to about 5 μg of polynucleotides are combined with about 8 nmol liposomes, and even more preferably about 1.0 μg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., GENE THERAPEUTICS: METHODS AND APPLICATIONS OF DIRECT GENE TRANSFER (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

2.1 Determination of a Therapeutically Effective Dose

The determination of a therapeutically effective dose of therapeutic agents identified by a screening method herein is well within the capability of those skilled in the art. A therapeutically effective dose refers to that amount of active ingredient which attenuates or eliminates TB infection contrasted to TB infection or attenuation that occurs in the absence of the therapeutically effective dose.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, an therapeutic agent reduces expression of an MTTGH gene or the activity of an MTTGH polypeptide by at least about 10, preferably about 50, more preferably about 75, 90, or 100% relative to the absence of the reagent. The effectiveness of the mechanism chosen to decrease the level of expression of an MTTGH gene or the activity of an MTTGH polypeptide can be assessed using methods well known in the art, such as hybridization of nucleotide probes to MTTGH-specific mRNA, quantitative RT-PCR, immunologic detection of an MTTGH polypeptide, or measurement of MTTGH activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects. Any of the therapeutic methods described above can be applied to any subject in need of such therapy.

3. Polypeptides

*M. tuberculosis* TG storage (MTTGH) polypeptides according to the invention comprise at least 12, 15, 25, 50, 75, 100, 125, 150, 175, 200, 225, 250 or 265 contiguous amino acids selected from the amino acid sequence shown in SEQ ID NO: 2, or a biologically active variant thereof, as defined below. A MTTGH polypeptide of the invention therefore can be a portion of an MTTGH protein, a full-length MTTGH protein, or a fusion protein comprising all or a portion of MTTGH protein.

3.1 Biologically Active Variants

MTTGH polypeptide variants which are biologically active, i.e., confer an ability by *M. tuberculosis* to store and/or process TG, also are considered MTTGH polypeptides for purposes of this application. Preferably, naturally or non-naturally occurring MTTGH polypeptide variants have amino acid sequences which are at least about 55, 60, 65, or 70, preferably about 75, 80, 85, 90, 96, 96, or 98% identical to the amino acid sequence shown in SEQ ID NO: 2 or a fragment thereof. Percent identity between a putative MTTGH polypeptide variant and an amino acid sequence of SEQ ID NO: 2 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of an MTTGH polypeptide can be found using computer programs well known in the art, such as DNASTAR software. Whether an amino acid change results in a biologically active MTTGH polypeptide can readily be determined by assaying for MTTGH activity, as described for example, in the specific Examples, below.

3.2 Fusion Proteins

In some embodiments of the invention, it is useful to create fusion proteins. By way of example, fusion proteins are useful for generating antibodies against MTTGH polypeptide amino acid sequences and for use in various assay systems. For example, fusion proteins can be used to identify proteins which interact with portions of an MTTGH polypeptide. Protein affinity chromatography or library-based assays for protein—protein interactions, such as the yeast two-hybrid or phage display systems, can be used for this purpose. Such methods are well known in the art and also can be used as drug screens.

A MTTGH polypeptide fusion protein comprises two polypeptide segments fused together by means of a peptide bond. For example, the first polypeptide segment can comprise at least 12, 15, 25, 50, 75, 100, 125, 150, 175, 200, 225, or 250 contiguous amino acids of SEQ ID NO: 2 or of a biologically active variant, such as those described above. The first polypeptide segment also can comprise full-length MTTGH protein.

The second polypeptide segment can be a full-length protein or a protein fragment. Proteins commonly used in fusion protein construction include galactosidase, glucuronidase, green fluorescent protein (GFP), autofluorescent proteins, including blue fluorescent protein (BFP), glutathione-5-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the MTTGH polypeptide-encoding sequence and the heterologous protein sequence, so that the MTTGH polypeptide can be cleaved and purified away from the heterologous moiety.

Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

3.3 Obtaining Polypeptides

MTTGH polypeptides can be obtained, for example, by purification of polypeptides from *M. tuberculosis*, expressed by of MTTGH polynucleotide(s) and other appropriate methods as will be appreciated by those skilled in the art in view of the teachings herein. In a specific example, the inventors have expressed poly His-tagged enzyme in *E. coli* and have purified it.

3.4 Protein Purification

MTTGH polypeptides can be purified from any cell which expresses the enzyme, including host cells which have been transfected with MTTGH enzyme expression constructs. A purified MTTGH enzyme polypeptide is separated from other compounds which normally associate with the MTTGH enzyme polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified MTTGH polypeptides is at least 80% pure; preferably, the preparations are 90%, 95%, or 99% pure. Purity of the preparations can be assessed by any means known in the art, such as SDS-polyacrylamide gel electrophoresis.

4. Polynucleotides

An MTTGH polynucleotide can be single- or double-stranded and comprises a coding sequence or the complement of a coding sequence for an MTTGH polypeptide. A coding sequence for MTTGH polypeptide of SEQ ID NO: 2 is shown in SEQ ID NO: 1.

Degenerate nucleotide sequences encoding MTTGH polypeptides, as well as homologous nucleotide sequences which are at least about 50, 55, 60, 65, 60, preferably about 75, 90, 96, or 98% identical to the nucleotide sequence shown in SEQ ID NO: 1 also are triaglycerol synthase-like enzyme polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of MTTGH polynucleotides which encode biologically active MTTGH polypeptides also are MTTGH polynucleotides.

4.1 Identification of Polynucleotide Variants and Homologs

Variants and homologs of the MTTGH polynucleotides described above also are MTTGH polynucleotides. Typically, homologous MTTGH polynucleotide sequences can be identified by hybridization of candidate polynucleotides to known MTTGH polynucleotides under stringent conditions, as is known in the art. For example, using the following wash conditions: 2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each homologous sequences can be identified which contain at most about 25-30% basepair mismatches. More preferably, homologous nucleic acid strands contain 15-25% basepair mismatches, even more preferably 5-15% basepair mismatches.

Species homologs of the MTTGH polynucleotides disclosed herein also can be identified by making suitable probes or primers and screening cDNA expression libraries. It is well known that the Tm of a double-stranded DNA decreases by 1-1.5° C. with every 1% decrease in homology (Bonner et al., J. Mol. Biol. 81, 123 (1973). Variants of MTTGH polynucleotides or polynucleotides of other species can therefore be identified by hybridizing a putative homologous MTTGH polynucleotide with a polynucleotide having a nucleotide sequence of SEQ ID NO: 1 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to MTTGH polynucleotides or their complements following stringent hybridization and/or wash conditions also are MTTGH polynucleotides. Stringent wash conditions are well known and understood in the art and are disclosed, for example, in Sambrook et al., MOLECULAR CLONING: A LABORATORY MANUAL, $2^{nd}$ ed., 1989, at pages 9.50-9.51.

Typically, for stringent hybridization conditions a combination of temperature and salt concentration should be chosen that is approximately 12-20° C. below the calculated $T_m$ of the hybrid under study. The $T_m$ Of a hybrid between an MTTGH polynucleotide having a nucleotide sequence shown in SEQ ID NO: 1 or the complement thereof and a polynucleotide sequence which is at least about 50, preferably about 75, 90, 96, or 98% identical to one of those nucleotide sequences can be calculated, for example, using the equation of Bolton and McCarthy, Proc. Natl. Acad. Sci. U.S.A. 48, 1390 (1962):

$$T_m=81.5°\text{ C.}-16.6(\log_{10}[Na^+])+0.41(\%\ G+C)-0.63(\%\ \text{formamide})-600/l),$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

4.2 Preparation of Polynucleotides

A naturally occurring MTTGH polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated MTTGH polynucleotides. For example, restriction enzymes and probes can be used to isolate polynucleotide fragments which comprises MTTGH nucleotide sequences. Isolated polynucleotides are in preparations which are free or at least 70, 80, or 90% free of other molecules.

MTTGH DNA molecules can be made with standard molecular biology techniques, using MTTGH mRNA as a template. MTTGH DNA molecules can thereafter be replicated using molecular biology techniques known in the art and disclosed in manuals such as Sambrook et al. (1989). An amplification technique, such as PCR, can be used to obtain additional copies of polynucleotides of the invention. The inventors have successfully demonstrated this approach.

Alternatively, synthetic chemistry techniques can be used to synthesize MTTGH polynucleotides. The degeneracy of the genetic code allows alternate nucleotide sequences to be synthesized which will encode a MTTGH polypeptide having, for example, an amino acid sequence shown in SEQ ID NO: 2 or a biologically active variant thereof.

4.3 Expression of Polynucleotides

To express a MTTGH polynucleotide, the polynucleotide can be inserted into an expression vector which contains the necessary elements for the transcription and translation of the inserted coding sequence. Methods which are well known to those skilled in the art can be used to construct expression vectors containing sequences encoding MTTGH polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a MTTGH enzyme polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those nontranslated regions of the vector enhancers, promoters, 5' and 3' untranslated regions which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding an MTTGH polypeptide, vectors based on SV40 or EBV can be used with an appropriate selectable marker.

5. Host Cells

According to certain embodiments of the subject invention, an MTTGH polynucleotide will need to be inserted into a host cell, for expression, processing and/or screening. A host cell strain can be chosen for its ability to modulate the expression of the inserted sequences or to process the expressed MTTGH polypeptide in the desired fashion. Such modifications of the polypeptide include, but are not limited to, acetylation, carboxylation, glycosylation, phosphorylation, lipidation, and acylation. Posttranslational processing which cleaves a "prepro" form of the polypeptide also can be used to facilitate correct insertion, folding and/or function. Different host cells which have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high yield production of recombinant proteins. For example, cell lines which stably express MTTGH polypeptides can be transformed using expression vectors which can contain viral origins of replication and/or endogenous expression elements and a selectable marker gene on the same or on a separate vector. Following the introduction of the vector, cells can be allowed to grow for 12 days in an enriched medium before they are switched to a selective medium. The purpose of the selectable marker is to confer resistance to selection, and its presence allows growth and recovery of cells which successfully express the introduced MTTGH sequences. Resistant clones of stably transformed cells can be proliferated using tissue culture techniques appropriate to the cell type. See, for example, ANIMAL CELL CULTURE, R. I. Freshney, ed., 1986.

5.1 Detecting Expression

A variety of protocols for detecting and measuring the expression of a MTTGH polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a MTTGH polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 12111216, 1983).

5.2 Expression and Purification of Polypeptides

Host cells transformed with nucleotide sequences encoding MTTGH polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode MTTGH polypeptides can be designed to contain signal sequences which direct secretion of soluble MTTGH polypeptides through a prokaryotic or eukaryotic cell membrane or which direct the membrane insertion of membrane-bound MTTGH polypeptide.

6. Antibodies

Antibodies are referenced herein and various aspects of the subject invention utilize antibodies specific to MTTGH polypeptide(s). As described above, one example of a therapeutic agent may pertain to an antibody. Any type of antibody known in the art can be generated to bind specifically to an epitope of an MTTGH polypeptide. "Antibody" as used herein includes intact immunoglobulin molecules, as well as fragments thereof, such as Fab, $F(ab')_2$, and Fv, which are capable of binding an epitope of an MTTGH polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of an MTTGH polypeptide can be used therapeutically, as mentioned, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody which specifically binds to the immunogen. Antibodies useful for embodiments of the subject invention may be polyclonal, but are preferably monoclonal antibodies.

7. Ribozymes

Ribozymes may be one category of test compounds potentially useful as therapeutic agents for treatment of TB infection. Ribozymes are RNA molecules with catalytic activity. See, e.g., Cech, Science 236, 15321539; 1987; Cech, Ann. Rev. Biochem. 59, 543568; 1990, Cech, Curr. Opin. Struct. Biol. 2, 605609; 1992, Couture & Stinchcomb, Trends Genet. 12, 510515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

Accordingly, another aspect of the invention pertains to using the coding sequence of a MTTGH polynucleotide to generate ribozymes which will specifically bind to mRNA transcribed from the MTTGH polynucleotide. Methods of designing and constructing ribozymes which can cleave other RNA molecules in trans in a highly sequence specific manner have been developed and described in the art (see Haseloff et al. Nature 334, 585591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a MTTGH RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate MTTGH RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease MTTGH expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors which induce expression of a target gene. Ribozymes also can be engineered to provide an additional level of regulation, so that destruction of mRNA occurs only when both a ribozyme and a target gene are induced in the cells.

8. Long Chain TG Hydrolase Activity in *Mycobacterium tuberculosis*

8.1 Materials and Methods

Bacterial Strains and Culture Conditions—*M. tuberculosis* H37Rv (ATCC 25618) and Δ-lipY mutant were grown in Middlebrook 7H9 (supplemented with 0.05% Tween 80, 10% oleic acid-albumin-dextrose-catalase enrichment, and 0.2% glycerol) and in Dubos-Tween 80-albumin medium (prepared from Dubos broth base and Dubos medium albumin as per the manufacturer's instructions). All media were purchased from Difco. *E. coli* DH5α and BL21 Star (DE3) (Invitrogen) used as host strains for cloning and expression experiments were grown on Luria-Bertani broth or agar and, when required, antibiotics were added to the culture media at the following concentrations: carbenicillin or kanamycin, 50 μg/ml; hygromycin B, 150 μg/ml for *E. coli* or 75 μg/ml for *M. tuberculosis*. Other chemicals and antibiotics were from Sigma Chemical Co., Fisher Scientific and Calbiochem. DNA restriction and modifying enzymes were procured from New England Biolabs (Beverly, Mass.).

Induction of lipase genes and TG utilization in *M. tuberculosis* strains under nutrient starvation after hypoxic stress—*M. tuberculosis* H37Rv and Δ-lipY mutant cells were grown under a hypoxic condition essentially as previously described to induce the accumulation of TG inside the mycobacterial cell (7). *M. tuberculosis* cells were inoculated into Middlebrook 7H9, grown aerobically at 37° C. in roller bottles to an $OD_{600}$ of 0.8 and were used to inoculate Dubos-Tween-albumin medium to an $OD_{600}$ of 0.015, grown up to an $OD_{600}$ of 0.06 and distributed in tubes or in single neck wolf bottles (Chemglass) with a 0.5 head space to culture volume ratio, sealed with rubber sleeve caps and slowly stirred on a magnetic stirrer for hypoxic growth up to 12 days. Harvested cells were divided into three sets. The first set was preserved in −80° C. and was used as control (0 h). The harvested cells of the second set were washed and resuspended in phosphate-buffered saline (PBS) and incubated at 37° C. for 6 h. The cells of the third set were washed, resuspended in normal 7H9-OADC-Tween (7H9) medium instead of PBS and served as a nutrient supplemented control. These differentially treated cells were used to measure induction of lipase gene transcripts by semi-quantitative RT-PCR and to measure the utilization of stored TG. RNA isolation and semi quantitative RT-PCR were performed as described before (7), using the primers shown in Table 1.

Cells from the three sets were autoclaved and total lipids were extracted with chloroform:methanol (2:1; v/v) as previously described (7). The 12 days old wild type *M. tuberculosis* hypoxic culture (10 ml) was also used for labeling with 1 μCi of [$^{14}$C]oleic acid (specific activity, 55 Ci/mole; American Radiolabeled Chemicals) for 1 h and then the cells were washed with PBS before incubating in PBS for the next 6 h. Lipids were analyzed by silica gel thin-layer chromatography (TLC) using n-hexane:diethyl ether (9:1; v/v), and the radioactivity in the silica gel corresponding to the TG band was measured using a liquid scintillation counter (Packard). An autoradiogram of the TLC was prepared. The amount of TG was visualized by dichromate/sulfuric acid charring of the TLC plates as described before (15). The charred TLC plate was also scanned for quantification of TG accumulation by using the AlphaImager 2200 Gel Doc system (AlphaInnotech).

Generation of lipY disrupted mutant of *M. tuberculosis* H37Rv—The lipY gene was disrupted by allelic exchange using specialized transducing phage as described (16). The disruption construct of lipY was made by sequential cloning of a 953-bp 5'-flank (consisting of the first 38 bp of lipY ORF and 915 bp sequence upstream of lipY ORF) and a 789-bp 3'-flank (consisting of last 4 bp of lipY ORF and 785 bp sequence downstream of lipY) of lipY, on either side of res-hyg-res gene cassette in the cosmid pYUB854. The two flanks were generated by PCR amplification using *M. tuberculosis* H37Rv genomic DNA as template by introducing AflII and XbaI and HindIII and SpeI sites on the ends of the 5'-flanks and 3'-flanks respectively for directional cloning into pYUB854 (Table-2). The PacI digested recombinant pYUB854 containing lipY disruption construct was introduced in phasmid phAE159 and the recombinant transducing phage obtained after packaging was used to transduce *M. tuberculosis*. LipY disruption by allelic exchange was confirmed by PCR analyses using specific sets of primers and Southern hybridization (Table-2). Ten hygromycin resistant clones were screened by PCR using a set of primers (Δ-F and Δ-R) designed from the deleted part of the lipY gene. The allelic exchange by double cross-over was confirmed with two sets of primers, each representing a outwardly directed hyg primer (H1 and H2) and a primer (primers E and F) in the mycobacterial genome beyond the flanking gene sequences used for making the homologous arms of the disruption construct.

DNA isolation and Southern blotting—Mycobacterial genomic DNA was isolated by the guanidine thiocyanate (GTC) method as described (17). DNA samples were digested with suitable restriction enzyme, separated by electrophoresis in 1% agarose gel, transferred to Nylon membranes (Nytran Plus, Schleicher and Schuell, Keen, N.H.) and hybridized with [α-$^{32}$P]dCTP labeled probes. Probe labeling and preparation were performed using rediview [α-$^{32}$P]dCTP and rediprime II random priming labeling kit (Amersham Biosciences) as per manufacturer's instructions.

Cloning and Expression of *M. tuberculosis* lipase/esterase genes in *E. coli*—The 24 open-reading frames (ORFs) were amplified from the genomic DNA of *M. tuberculosis* H37Rv by PCR using Pfu Turbo Hotstart DNA polymerase (Stratagene) and cloned into pET200 D-TOPO expression vector (Invitrogen). The directionally cloned fragments were completely sequenced to confirm the sequence integrity of each expression construct. The constructs were used to transform competent cells of *E. coli* BL21 Star (DE3) (Invitrogen) and the proteins were expressed as N-terminal 6× His-tagged (SEQ ID NO: 79) fusion proteins after induction with IPTG according to the manufacturer's protocols. Total cell lysates from induced cultures were prepared in 0.1 M Tris.HCl pH 8.0 containing 1 mM DTE and used for screening for TG hydrolase activity of all lip gene products. Untransformed host cell lysate was used as control.

Solubilization and purification of LIPY—In our attempts to produce soluble LIPY protein, we performed IPTG induction in *E. coli* BL21 Star (DE3) cells at 16° C., 24° C. and 37° C. for 4 h and 12 h. Inductions were also carried out without using IPTG in Dual Media (Zymo Research). In all cases virtually all the expressed protein was insoluble. To solubilize the insoluble protein, his-tagged LIPY was expressed in 500 ml cultures by induction with 1 mM IPTG at 37° C. for 12 h in LB broth. Total cell lysates were centrifuged at 10,000×g and the pellet was solubilized in a buffer containing 1% (w/v) sodium lauroyl sarcosine, 2 mM sodium dodecyl sulfate (SDS), 25 mM triethanolamine, 1.5 mM $CaCl_2$, 50 mM sodium phosphate buffer pH 7.0, 300 mM NaCl and 50 μg/ml aprotinin with shaking at 330 rpm at 10° C. for 1 h. The solution was clarified by centrifugation at 16,000×g for 20 min at 4° C. and the supernatant was loaded onto a 5 ml bed-volume cobalt-affinity resin (TALON, BD Biosciences). Unbound proteins and detergents were removed by washing the resin with 10 bed-volumes of bind/wash buffer (50 mM sodium phosphate buffer pH 7.0, 300 mM NaCl) followed by 10 bed-volumes of bind/wash buffer containing 10 mM imidazole. The bound protein was eluted in 5 bed-volumes of bind/wash buffer containing 150 mM imidazole followed by 5 bed-volumes of bind/wash buffer containing 250 mM imidazole and 5 ml fractions were collected. Aliquots of fractions collected at each step of the solubilization and purification process were analyzed on 12% SDS-PAGE followed by coomassie staining.

Lipase Assays—Lipase activity was measured by the release of [$^{14}$C]oleic acid from [$^{14}$C]triolein (55 mCi/mmol, American Radiolabeled Chemicals) using a modified method of Belfrage and Vaughan (18). The reaction mixture contained 50-100 μg protein from total cell lysates, 0.2 μCi [$^{14}$C] triolein, 20 mM triolein, 2% gum arabic, 1 μg bovine serum albumin, 100 mM NaCl and 0.1 M Tris.HCl pH 8.0 in a total volume of 100 μl. Triolein was emulsified in gum arabic and aliquoted into the reaction mixture at the indicated concentrations prior to the addition of enzyme. After incubation at 37° C. for 2 h, the reaction mixture was extracted with 1 ml chloroform:methanol:hexane (1.25:1.41:1, v/v/v) following the addition of 200 μl 0.1 M $NaHCO_3$, pH 10.5. The radioactivity released into the upper aqueous phase was measured by liquid scintillation counting. Alternatively, the reaction mixture was acidified with 50 μl 6 N HCl and extracted with 1 ml chloroform:methanol (2:1, v/v). The lipids in the lower organic phase was resolved on silica TLC plates developed in hexane:diethyl ether:acetic acid (65:35:2, v/v/v) and the radioactivity corresponding to the internal oleic acid standard was determined by liquid scintillation counting.

To investigate substrate specificity, sonicated emulsions of 20 mM [$^{14}$C]diolein or [$^{14}$C]dioleoyl phosphatidylcholine or [$^{14}$C]dioleoyl phosphatidylethanolamine or [$^{14}$C]hexadecylpalmitate were used. To measure pH stability, the purified enzyme was pre-incubated in the appropriate buffer for 15 min at 24° C. prior to the assay at 37° C. for 2 h. Temperature stability was measured by pre-incubating purified LIPY at the indicated temperature for 15 min prior to assay at 37° C. The effects of serine-directed reagents like diethyl-p-nitrophenyl phosphate (E-600), phenylmethanesulfonyl fluoride (PMSF), detergents like SDS, polyethylene glycol tert-octylphenyl ether (Triton X-100), polyethylene glycol sorbitan monolaurate (Tween-20) and various salts were determined by pre-incubating the purified LIPY for 15 min at 24° C. with the indicated concentration of effector prior to the assay at 37° C. for 2 h.

8.2 Results

Identification and cloning of *M. tuberculosis* lipase/esterase genes—*M. tuberculosis* probably uses fatty acids as a carbon source during its dormancy inside the host (8, 10). Previously, we identified 15 tgs genes in the genome of the pathogen several of which are induced under culture conditions that lead to a dormancy-like state resulting in TG accumulation within the bacterial cell (7). Utilization of stored TG would require a true lipase. However no mycobacterial gene that encodes long-chain TG hydrolase has been identified and characterized. We screened the *M. tuberculosis* genome for the presence of genes encoding such enzymes. The *M. tuberculosis* genome contains 21 ORFs annotated as putative lipase/esterase genes. We used the sequence of a putative TG lipase from *M. tuberculosis* strain W17 in the NCBI database (U76006.1, Acc. No. NCBI AAB18414, Bifani et al) to screen the *M. tuberculosis* H37Rv genome for homologous genes. This approach identified three additional ORFs—Rv1169c, Rv3097c and Rv1834, that we designate as lipX, lipY and lipZ respectively, to be consistent with the present nomenclature of all the other lip genes in the *M. tuberculosis* genome. We included these three genes along with the 21 previously annotated 'lip' genes in our screen for genes encoding true lipases.

Screening of *M. tuberculosis* lipase/esterase gene products for long-chain TG hydrolase activity—The 24 selected *M. tuberculosis* ORFs encoding putative lipase/esterase proteins were expressed in *E. coli* and total cell lysates were assayed for triolein hydrolase activity. Lipase activity above untransformed control was normalized for the expression level of each recombinant protein in the total cell lysate. Triolein hydrolase activity in our standard radiometric assay at pH 8.0 was by far the highest in the lysates of recombinant *E. coli* expressing LIPY followed by LIPK, LIPL and LIPC that showed much lower activities followed by lysates expressing LIPX and LIPG that had even lower levels of activity. All other lip gene products showed little or no triolein hydrolase activity (Table 3).

Utilization of stored TG and induction of lipase genes by starvation in *M. tuberculosis* cells grown under hypoxic conditions—In order to test the hypothesis that lipase(s) release fatty acids from TG stores under nutrient-deprived conditions that might be encountered during dormancy, we cultured *M. tuberculosis* under hypoxic conditions for 12 days, a condition which was previously shown to cause TG accumulation (7), and subsequently incubated these cells in a starvation medium (PBS) to test whether the stored TG was utilized under such conditions. To label the stored TG, we incubated *M. tuberculosis* cells held under hypoxia for 12 days with $^{14}$C-oleic acid for 1 h and then the labeled cells were incubated in PBS for 6 h. After incubation, about 50% of the labeled TG was utilized under nutrient deprived condition (FIG. 1A). Accumulation of TG during hypoxia and utilization during starvation was also clearly seen by dichromate/sulfuric acid charring of the silica gel-TLCs of the total lipids (FIG. 1B). The intensity of the TG band showed about 50% decrease after 6 h of incubation in PBS. Cells incubated in nutrient rich medium, used as a control, did not utilize significant amounts of the stored TG (FIG. 1C).

Figure 2:
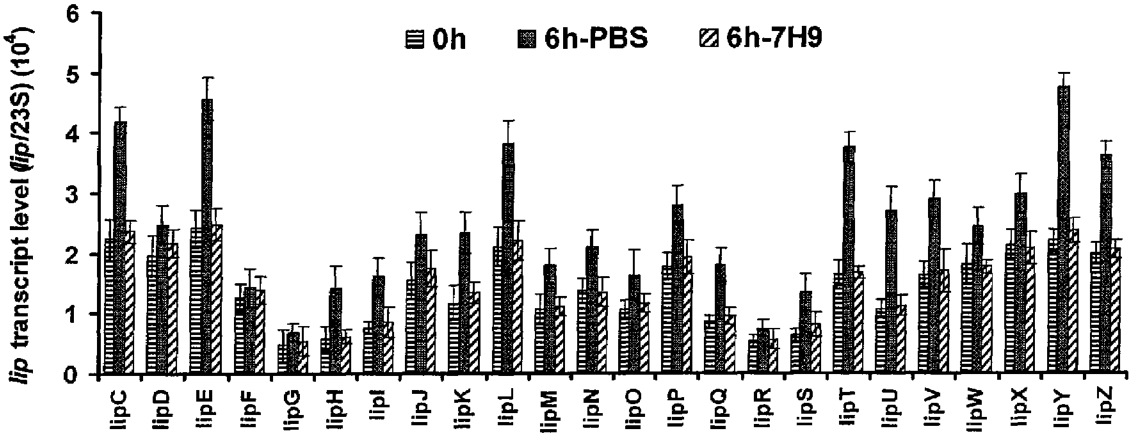
FIG. 2: RT-PCR assessment of the induction of lip genes upon starvation (A) and estimation of the potential contribution to TG hydrolysis (B). *M. tuberculosis* H37Rv was incubated in PBS or in 7H9 medium for 6 h after TG accumulation by hypoxic growth for 12 days. Transcript levels of lips are shown as a fraction of 23S rRNA transcripts (mean±SD from three independent experiments). The methods used for quantitation and experimental details are given in Experimental Procedures. In B, the potential relative contribution of each lip gene product to the total lipase activity was estimated by multiplying transcript level with the lipase activity of each gene product expressed in *E. coli*.
Figure 2:
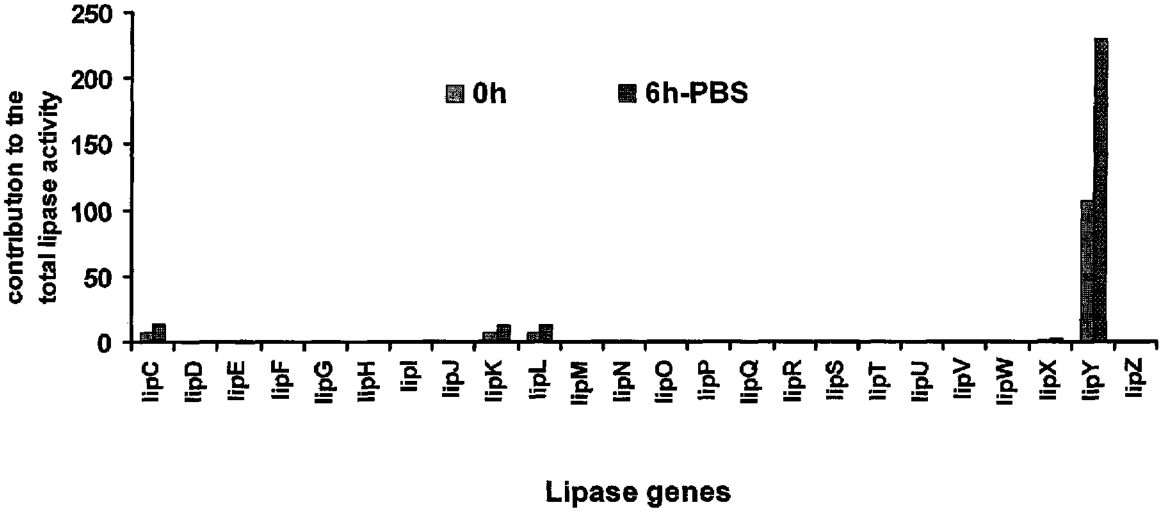

During the TG utilization conditions, the lipase genes involved in the release of fatty acids from TG would be expected to be induced. To test for this possibility, the transcript levels of all the 24 selected ORFs were measured by semi-quantitative RT-PCR analyses. The transcript level of each lip gene before starvation (0 h), after starvation (6 h-PBS) and after incubation in nutrient rich medium (6 h-7H9) are expressed as a fraction of the 23S rRNA transcript level of the same sample (FIG. 2A). Most of the lipase genes showed induction of transcript level during incubation for 6 h in PBS. The highest level of induction after 6 h starvation was seen in the transcripts of lipY, lipE, lipC, lipZ lipL and lipT. Since the lip gene products manifested very different degrees of TG hydrolase activity, the possible relative contributions of the lipase genes to the hydrolysis of stored TG within the mycobacterial cell were assessed by multiplying the transcript level after 6 h starvation with the triolein hydrolase activity of each expressed gene product. Such an analysis showed that LIPY had by far the greatest potential for hydrolyzing in vivo stores of TG in the mycobacterium under such conditions (FIG. 2B).

Figure 3:
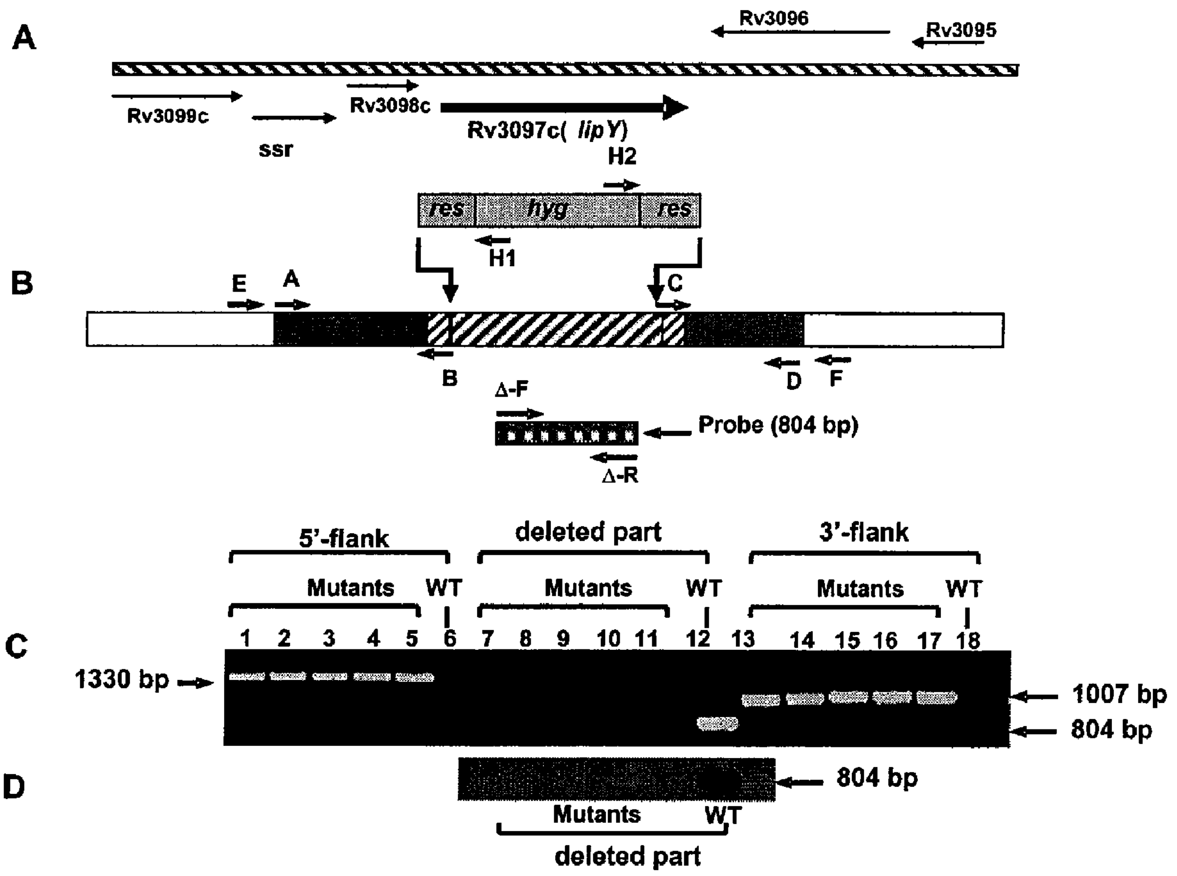
FIG. 3: Generation of a lipY deficient mutant of *M. tuberculosis*. (A) Genomic organization of lipY (Rv3097c). (B) Schematic representation of the disruption construct for lipY. A hatched region with grey flanks depicts the genome sequence of lipY and its flanking regions used to make the disruption construct. Primer pairs A/B and C/D were used to generate the 5'- and 3'flanks of the disruption construct. The part of the lipY gene (upward diagonal hatch) replaced with res-hyg-res gene cassette is shown. Primer pairs E/H1, H2/F, and □-F/□-R (solid square check box) were used for PCR analysis of homologous recombination as described in the text. (C) PCR analysis of 5'-flank (lanes: 1-5, Δ-lipY mutants; 6, wild type), deleted part of the gene (lanes: 7-11, Δ-lipY mutants; 12, wild type) and 3'-flank (lanes: 13-17, Δ-lipY mutants; 18, wild type). (D) Southern blot hybridization of five Δ-lipY mutant clones and wild type probed with the part of the deleted sequence of lipY. WT, wild type

Disruption of lipY in *M. tuberculosis*—LIPY showed the highest capacity to hydrolyze long chain TG among all the probable lipase gene products of *M. tuberculosis* cloned and expressed in *E. coli*. Moreover, when the organism was subjected to a nutrient deprived state after the cells had accumulated TG under hypoxia, lipY was found to be the most highly induced gene. These results suggested that LIPY is most likely to be the major lipase involved in the hydrolysis of the stored TG. To test for this possibility, we generated a lipY knock-out mutant of *M. tuberculosis* (FIG. 3). lipY was disrupted by allelic exchange using specialized transducing recombinant mycobacteriophage phAE159 (16). In the constructed lipY deletion allele, 1258 bp out of 1314 bp of total lipY gene sequence was replaced with a hygromycin resistance gene cassette (res-hyg-res) flanked by res (resolvase recognition sequence) sequences. Several mutants were identified as tentative lipY disrupted mutant (Δ-lipY) as an 804-bp sequence in the deleted lipY-segment could not be amplified by PCR (FIG. 3C). Further PCR analysis of the flanking regions of the deleted part of the gene confirmed the deletion at the correct orientation by homologous recombination (FIG. 3C). A 1330-bp 5'-flank (primer pair–E+H1) and a 1007-bp 3'-flank (primer pair–H2+F) could be amplified from the selected disputants, but, no product could be amplified from the wild type genomic DNA (FIGS. 3B, C). Southern blot of EcoRI restricted genomic DNA of five putative ΔlipY mutants when hybridized with a 804-bp probe generated from the deleted sequence of the gene didn't show any hybridization where as the wild type control showed the hybridized band (FIG. 3D). lipY transcript was absent in Δ-lipY mutant and the level of induction of the transcripts of the other lip genes was similar in the Δ-lipY and the wild type, when both were incubated in PBS or in 7H9 medium (data not shown) was confirmed by RT-PCR (data not shown).

TG utilization by lipY deficient mutant of *M. tuberculosis*—*M. tuberculosis* wild type and Δ-lipY mutant cells were subjected to TG utilizing condition as described above. When subjected to starvation by incubating in PBS, TG utilization in lipY mutant was drastically decreased, compared to that in the wild type (FIG. 1C). Also no significant TG hydrolysis could be detected when the cells were incubated in a nutrient rich medium (7H9) as a control.

Figure 4:
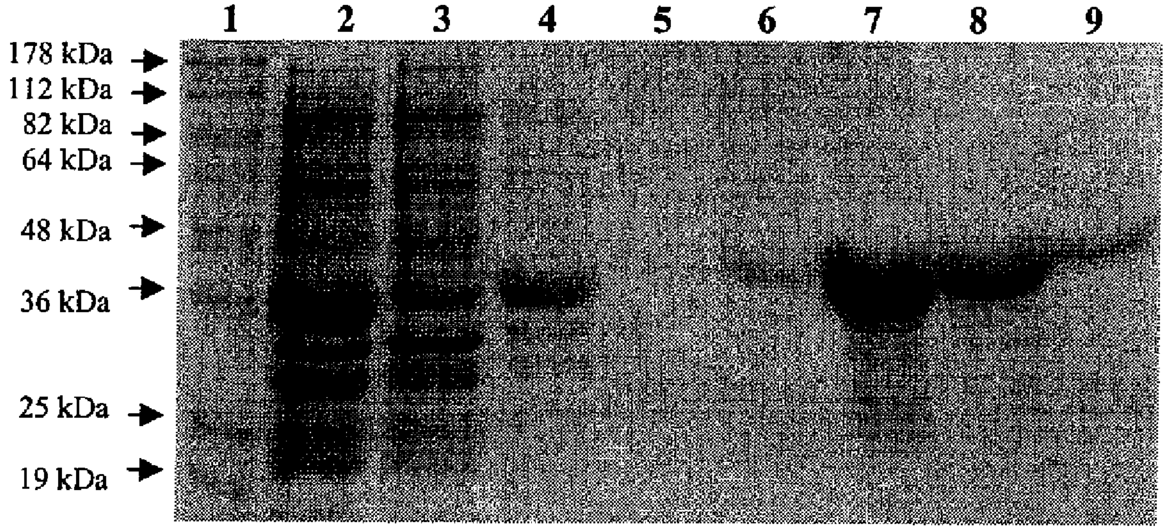
FIG. 4: SDS-PAGE analysis of the expression and purification of LIPY. His-tagged LIPY was expressed in *E. coli* BL21 cells, solubilized from the 16,000×g pellet from cell lysate and purified by cobalt affinity chromatography (TALON) as described in Experimental Procedures. Protein samples were loaded on a 12% SDS-polyacrylamide gel under reducing conditions. Lane 1, Benchmark prestained molecular weight markers (Invitrogen); lane 2, 16,000×g supernatant from solubilized inclusion bodies; lane 3, flow-through fraction from TALON resin; lanes 4-5, 10 mM imidazole wash; lanes 6-9, 150 mM imidazole eluted fractions.

Purification of LIPY—Since LIPY showed the highest potential for hydrolyzing the TG stored inside the *M. tuberculosis* cell, we purified LIPY and characterized its activity. LIPY was expressed as a 6× his-tagged (SEQ ID NO: 79) fusion protein in *E. coli* at 16° C., 24° C. and 37° C. under various conditions of induction and was found to partition into the 16,000×g pellet after cell lysis in all cases. Therefore, we solubilized LIPY from this pellet using a low concentration of detergents that did not inhibit the activity of LIPY as determined by preliminary assays with total cell lysates containing recombinant LIPY (data not shown). The clarified supernatant from the solubilized 16,000×g pellet contained a large quantity of recombinant LIPY (FIG. 4, lane 2) and was used to purify LIPY by cobalt-affinity chromatography. The 6× his-tagged (SEQ ID NO: 79) LIPY protein was bound to the TALON resin and was eluted in the 150 mM imidazole elution step (FIG. 4). The recombinant LIPY migrated on SDS-PAGE with an apparent molecular weight that was slightly lower than the theoretically predicted value of 45 kDa. The purified enzyme eluted from a pre-calibrated Superose-6 gel-filtration column just after the void volume suggesting that the purified, recombinant LIPY exists as aggregates (data not shown).

Figure 5:
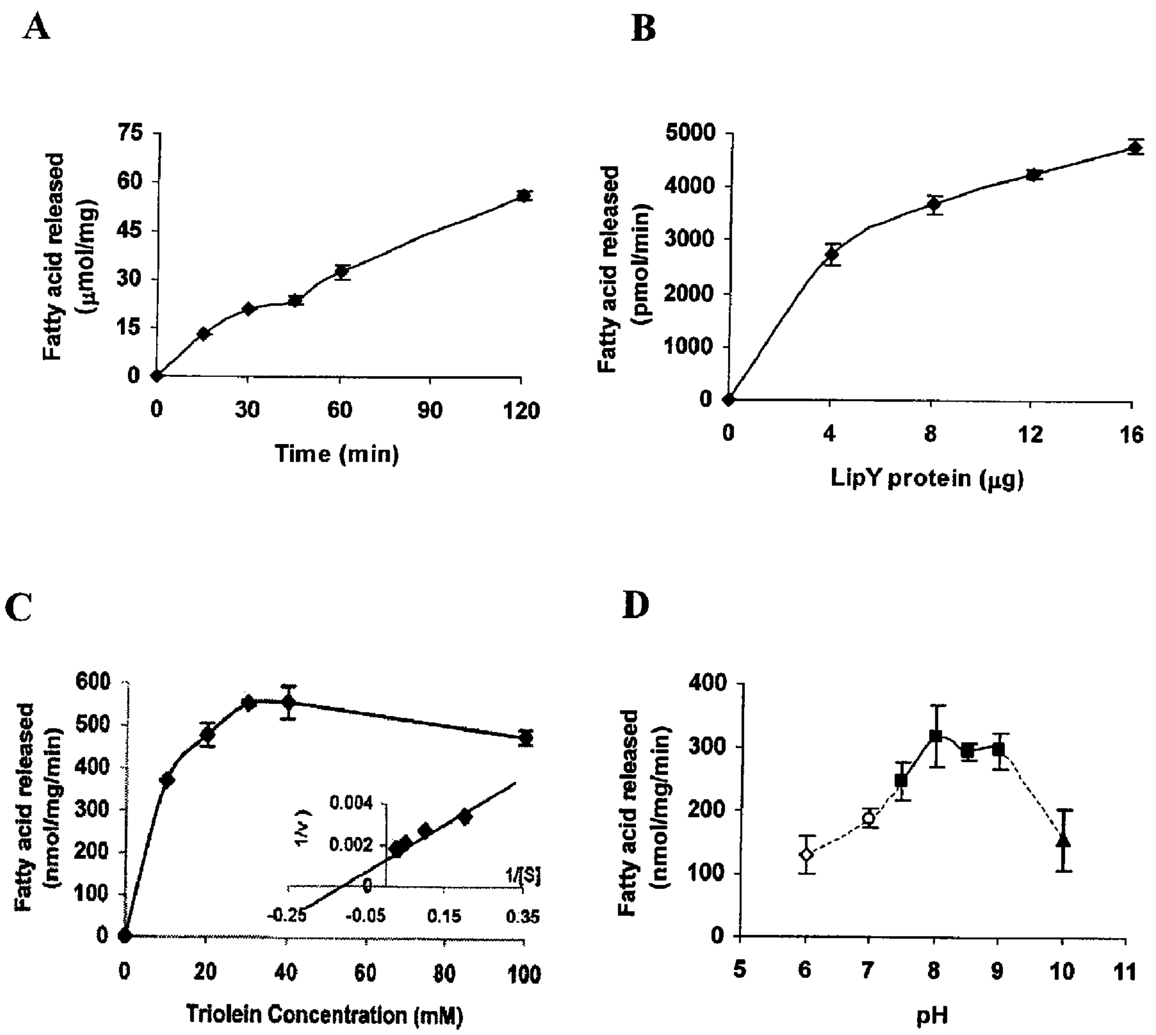
FIG. 5: Characterization of triolein hydrolase activity of purified LIPY. A) Time-course of [$^{14}$C]triolein hydrolysis at pH 8.0 was determined using 8 μg of purified LIPY protein per assay. B) protein concentration dependence of TG hydrolysis (incubation time, 2 h) C) substrate concentration dependence of enzyme activity (incubation time, 2 h). D) Effect of pH on lipase activity. LIPY was incubated for 15 min at room temperature in 0.1 M citrate-phosphate buffer pH 6.0 or 0.1 M potassium phosphate buffer pH 7.0 or 0.1 M Tris-HCl pH 7.5/pH 8.0/pH 8.5/pH 9.0 or 0.1 M glycine-NaOH buffer pH 10.0 prior to the assay. Values are mean±SD for three replicates.
Figure 6:
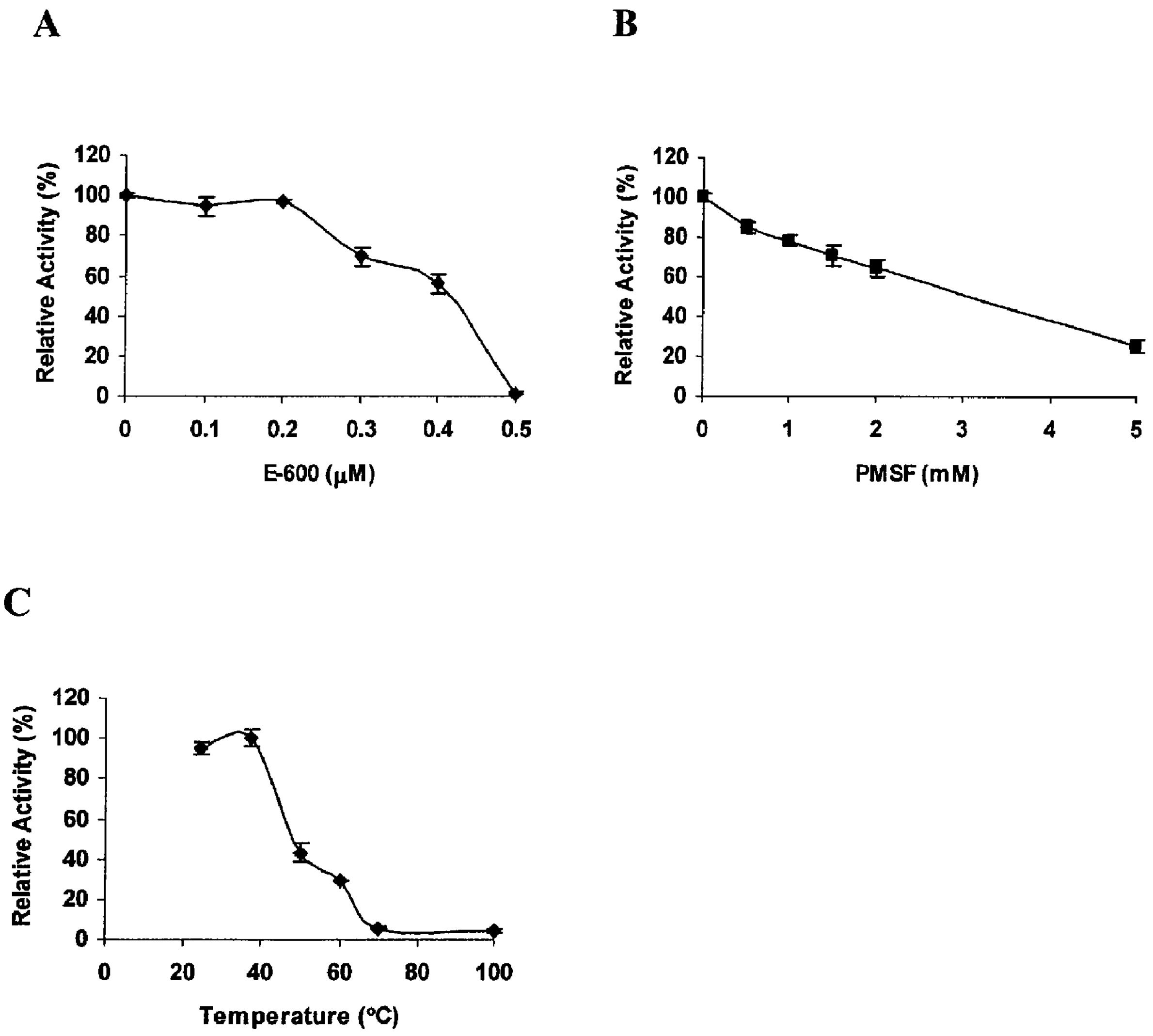
FIG. 6: Effect of E-600 (A), and PMSF (B), and temperature on TG hydrolysis by LIPY. LIPY was incubated with indicated concentration of inhibitor for 15 min at room temperature prior to assay at 37° C. In C, LIPY was incubated at indicated temperature for 15 min prior to assay. Values are mean±SD from three separate experiments.
Figure 7:
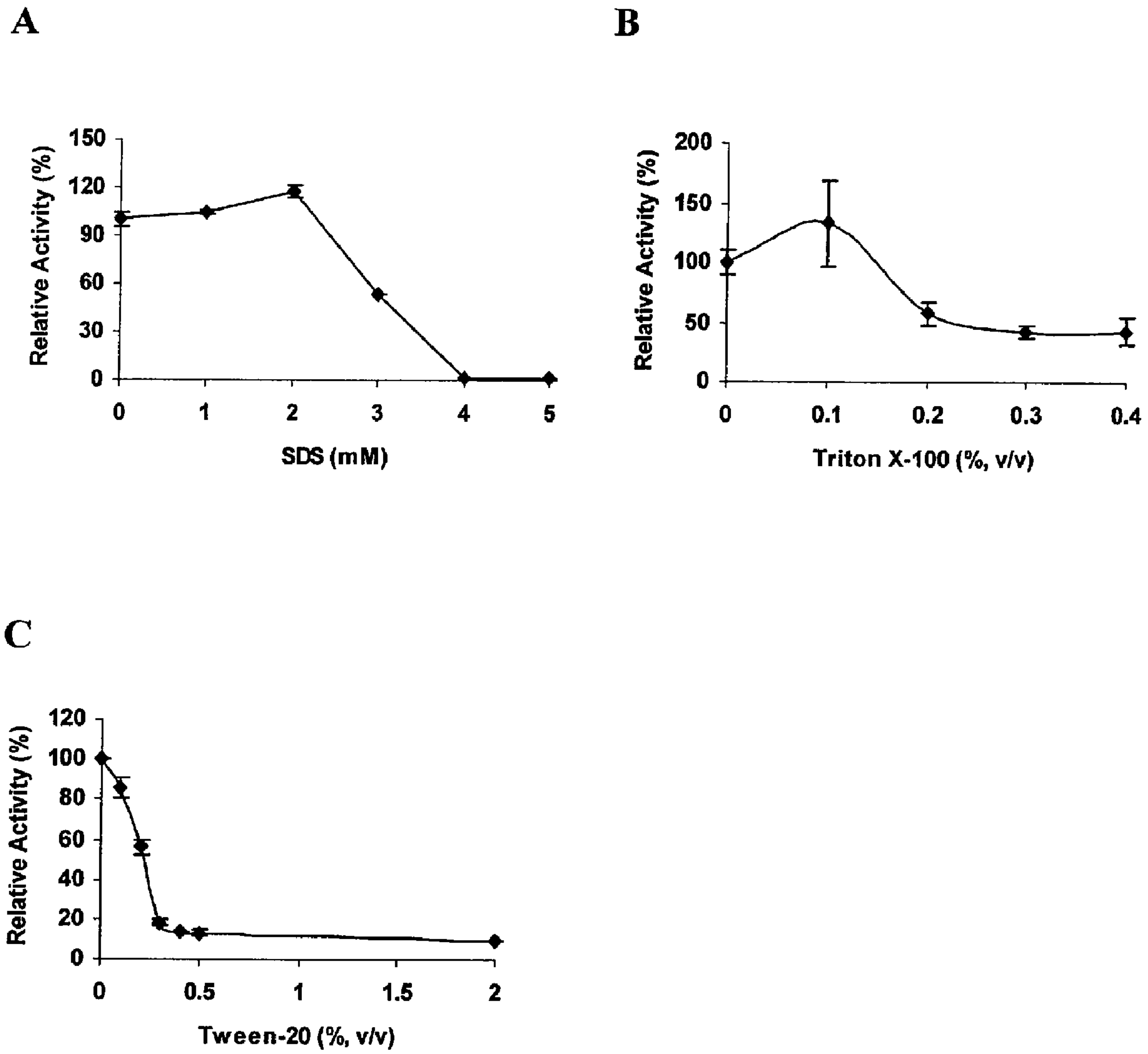
FIG. 7: Effect of detergents on LIPY activity. Purified LIPY was pre-incubated with the indicated concentrations of SDS (A), Triton X-100 (B) or Tween-20 (C) for 15 min at room temperature prior to assay. Activity relative to control is given as mean±SD from three replicates.

Biochemical characterization of the TG hydrolase activity of LIPY—The purified recombinant LIPY protein showed very high activity in our standard radiometric triolein hydrolysis assay. Lipase activity increased linearly with time and protein concentration (FIGS. 5A, B). LIPY displayed typical Michaelis-Menten kinetics (FIG. 5C) and the apparent $K_m$ and $V_{max}$ values were calculated to be 7.57 mM and 653.3 nmol/mg/min respectively from the rectilinear double-reciprocal plot. LIPY hydrolyzed [$^{14}$C]diolein at a lower rate (316.8±9.0 nmol/mg/min). LIPY did not show any fatty acid release when incubated with phosphatidylcholine, phosphatidyl ethanolamine or hexadecyl palmitate (data not shown). LIPY displayed optimal activity between pH 8.0 and pH 9.0 (FIG. 5D). The effect of inhibitors like E-600 which is an organophosphorous compound that irreversibly inhibits various esterases and is known to target serine esterases/lipases was tested on LIPY. E-600 inhibited LIPY by 99.5% at 0.5 μM (FIG. 6A) and PMSF at 5 mM inhibited LIPY activity by 75% (FIG. 6B). The temperature stability of LIPY was investigated by pre-incubation of the purified protein at the indicated temperature for 15 min. The lipase activity of LIPY dropped off sharply when the enzyme was held at 50° C. or higher (FIG. 6C). LIPY was very stable in storage and retained nearly all of its original activity even after 60 days at 4° C. and after 4 cycles of freezing at −20° C. followed by thawing. The effect of various detergents on LIPY was investigated. Lipase activity was stimulated slightly by SDS at concentrations up to 2 mM above which the activity was severely inhibited (FIG. 7A). Triton X-100 at 0.1% stimulated the activity but higher concentrations were inhibitory (FIG. 7B). The inhibition by SDS was partially reversed by Triton X-100 and 20% of the original activity was recovered (data not shown). Tween-20 inhibited LIPY at all concentrations from 0.1-2.0% (FIG. 7C). Many lipases require calcium for activity but LIPY was inhibited by $CaCl_2$. $CoCl_2$, $MnCl_2$, $ZnCl_2$, and $MgCl_2$ also inhibited the activity. However NaCl, KCl, sodium acetate and potassium acetate enhanced the activity (Table 4).

LIPY, a member of the HSL family-Thirteen of the 24 putative lipase/esterases can be classified as lipases belonging to the HSL family (12) and LIPY was the only protein out of the twenty-four with a putative TG hydrolase activity as annotated in the database (19). The product of lipY would encode a protein with a predicted molecular weight of 45 kDa and a p1 of 4.5. However, it showed only 9-21% global amino acid identity with the other lipase/esterase-like proteins in the mycobacterial genome (Table 5). Pair-wise alignment of the amino acid sequence of LIPY with 35 representative lipases from all the eight reported families of bacterial lipases (20) indicated that LIPY shared only 12-23% global amino acid identity with known bacterial lipases. However, LIPY possesses the conserved active-site motif GDSAG L(SEQ ID NO: 61 characteristic of the HSL family. Since the crystal structures of the *Bacillus subtilis* brefeldinA esterase and the *Archaeoglobus fulgidus* carboxylesterase which belong to the HSL family have been elucidated (21, 22), we used the Cn3D Version 4.1 software from the Entrez System at NCBI to produce a structure-based sequence alignment of LIPY with the members of the HSL family. The alignment of conserved domains produced by Cn3D was then used to align other selected members of the HSL family by ClustalW multiple sequence alignment program. The multiple sequence alignment output from ClustalW was then adjusted manually to achieve maximum similarity between the amino acid sequences. As shown in FIG. 8, this alignment revealed a high degree of similarity between the C-terminal half of LIPY and other members of the HSL family. This region of high similarity includes the catalytic domain with the consensus pentapeptide GDSAG (SEQ ID NO: 61) containing the active serine residue and the strictly conserved HGGG (SEQ ID NO: 68) motif of unknown function (23) located immediately upstream of the active site consensus motif. The aspartate and histidine residues of the active-site are also conserved with the other members of the HSL family.

REFERENCES

1. WHO Report. (2004) *WHO/HTM/TB/*2004.343
2. Dannenberg, Jr., A. M., and Rook G. A. W. (1994) In *Tuberculosis: Pathogenesis, Protection and Control*, Bloom, B. R., (Ed.) American Society of Microbiology, Washington D.C.
3. Honer zu Bentrup, K., and Russell D. G. (2001) *Trends Microbiol.* 9, 597-605
4. Dye, C., Scheele, S., Dolin, P., Pathania, V., and Raviglione M. C. (1999) *JAMA.* 282, 677-686
5. WHO Report. (2005) *WHO/HTM/TB/*2005
6. Zahrt, T. C. (2003). *Microbes Infect.* 5, 159-167
7. Daniel, J., Deb, C., Dubey, V. S., Sirakova, T. D., Abomoelak, B., Morbidoni, H. R., and Kolattukudy P. E. (2004) *J. Bacteriol.* 186, 5017-5030
8. Munoz-Elias, E. J., and McKinney, J. D. (2005) *Nat. Med.* 11, 638-644
9. Russell, D. G. (2003) *Nat. Cell Biol.* 5, 776-778
10. Segal, W., and Bloch H. (1956) *J. Bacteriol.* 72, 132-141
11. Cole S T, Brosch R, Parkhill J, Garnier T, Churcher C, Harris D, Gordon S V, Eiglmeier K, Gas S, Barry CE 3rd, Tekaia F, Badcock K, Basham D, Brown D, Chillingworth T, Connor R, Davies R, Devlin K, Feltwell T, Gentles S, Hamlin N, Holroyd S, Hornsby T, Jagels K, Krogh A, McLean J, Moule S, Murphy L, Oliver K, Osborne J, Quail M A, Rajandream M A, Rogers J, Rutter S, Seeger K, Skelton J, Squares R, Squares S, Sulston J E, Taylor K, Whitehead S, Barrell B G. (1998) *Nature* 393, 537-44
12. Hotelier, T., Renault, L., Cousin, X., Negre, V., Marchot, P., and Chatonnet A. (2004) *Nucleic Acids Res.* 32, D145-D147
13. Canaan, S., Maurin, D., Chahinian, H., Pouilly, B., Durousseau, C., Frassinetti, F., Scappuccini-Calvo, L., Cambillau, C., and Bourne Y. (2004) *Eur. J. Biochem.* 271, 3953-3961
14. Zhang, M., Wang, J-D., Li, Z-F., Xie, J., Yang, Y-P., Zhong, Y., and Wang, H-H. (2005) Protein Expr. Purif. 42, 59-66
15. Sirakova T. D., Thirumala A. K., Dubey V. S., Sprecher H., and Kolattukudy P. E. (2001) *J Biol. Chem.* 276, 16833-16839
16. Bardarov, S., Bardarov, Jr. S., Pavelka, Jr. M. S., Sambandamurthy, V, Larsen, M., Tufariello, J., Chan, J., Hatfull, G., and Jacobs, Jr., W. R. (2002). Microbiology. 148, 3007-3017
17. Derbyshire, K. M., and Bardarov, S. (2000). in *Molecular genetics of Mycobacteria* (G. F. Hatfull and W. R. Jacobs, Jr. eds) pp. 93-107, ASM Press, Washington, D.C.
18. Belfrage, P., and Vaughan M. (1969) *J Lipid Res.* 10, 341-344
19. http://au.expasy.org/cgi-bin/niceprot.pl?P77909
20. Arpigny, J. L., and Jaeger K-E. (1999) *Biochem. J.* 343, 177-183
21. Wei, Y., Contreras, J. A., Sheffield, P., Osterlund, T., Derewenda, U., Kneusel, R. E., Matern, U., Holm, C., and Derewenda Z. S. (1999) *Nature Struct. Biol.* 6, 340-345
22. De Simone, G., Menchise, V., Manco, G., Mandrich L., Sorrentino N., Lang, D., Rossi, M., and Pedone C. (2001) *J. Mol. Biol.* 314, 507-518
23. Jaeger, K-E., Dijkstra, B. W., and Reetz M. T. (1999) *Annu. Rev. Microbiol.* 53, 315-351
24. Vereecke, D., Cornelis, K., Temmerman, W., Holsters, M., and Goethals K. (2002) *Trends Microbiol.* 10, 485-488
25. Jackson, S. K., Stark, J. M., Taylor, S., and Harwood J. L. (1989) *Br. J. Exp. Path.* 70, 435-441
26. McCune, R. M., Feldmann, F. M., Lambert, H. P., and McDermott, W. (1966) *J Exp. Med.* 123, 445-468
27. Wayne, L. G., and Sohaskey, C. D. (2001) *Annu. Rev. Microbiol.* 55, 139-163
28. Voskuil, M. I., Schnappinger, D., Rutherford, R., Liu, Y., and Schoolnik, G. K. (2004) *Tuberculosis* (Edinb.) 84, 256-262
29. Betts, J. C., Lukey, P. T., Robb, L. C., McAdam, R. A., and Duncan K. (2002) *Mol. Microbiol.* 43, 717-731
30. Fisher, M. A., Plikaytis, B. B., and Shinnick, T. M. (2002) *J. Bacteriol.* 184, 4025-4032
31. Danelishvili, L., Poort, M. J., and Bermudez, L. E. (2004) *FEMS Microbiol Lett.* 239, 41-49
32. Paznokas, J. L., and Kaplan A. (1977) *Biochim. Biophys. Acta* 487, 405-421
33. Kolattukudy, P. E. (1984) In *Lipases*, Borgstrom, B., and Brockman, H., (Eds.) Elsevier Science Publishers, Amsterdam
34. Brennan, M. J., and Delogu G. (2002) *Trends Microbiol.* 10, 246-249

All patents, patent applications, publications, texts and references discussed or cited herein are incorporated by reference to the extent not inconsistent with the teachings herein. In addition, all terms not specifically defined are first taken to have the meaning given through usage in this disclosure, and if no such meaning is inferable, their normal meaning. Where a limitation is described but not given a specific term, a term corresponding to such limitation may be taken from any references, patents, applications, and other documents cited herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. Thus, for the above variations and in other regards, it should be understood that the examples and embodiments described herein are for illustrative purposes only and that various modifications or changes in light thereof will be suggested to persons skilled in the art and are to be included within the spirit and purview of this application and the scope of the appended claims.

*Mycobacterium tuberculosis* triacylglycerol hydrolase

TABLE 1

Primers used for RT-PCR analyses of transcripts of lipase genes induced in *M. tuberculosis* (SEQ ID NOS 3-50 respectively in order of appearance)

| Gene | Primer pairs (5'-3') |
|---|---|
| lipC (Rv022) | F: GGTAAGCACCTCAAGCCGCTCGGC<br>R: GCGCTGAACCACTACCCGCTCCAG |
| lipD (Rv1923) | F: GGTGTTCAGCGGGCGAGCGAGTTC<br>R: GGCGCAACCACGGTCACTCCTCAC |
| lipE (Rv3775) | F: CTAGACGCCGTGACGGCAACCGGC<br>R: ACTGGGCGCGACCAGCGGCACATC |
| lipF (Rv3487c) | F: CGACGGCGCTGGGCGGGTGGTGCT<br>R: CGCGCCACGGCTTGCGGCGCGAGGT |
| lipG (Rv0646c) | F: CTGATCATGGGCCTGGGCGCCCAG<br>R: GGACCCGTGAGCAGCGCCAGCAGC |
| lipH (Rv1399c) | F: GACCTTCACCGCGGCCGACGGTGTC<br>R: TGCGTGCAACGCCCTCTTCAGCGCC |
| lipI (Rv1400c) | F: GGGATCGAGGCCGTGCGCCAGCGGT<br>R: GCACAACCCGTAGCGCCACCAGCCC |
| lipJ (Rv1900c) | F: CGCACGGTCGAGGACACCAGCACC<br>R: ACCCGGTAGGCGCCCAGGTTCGTC |
| lipK (Rv2385) | F: GCCAGACGGGCCGTGGGGGATATG<br>R: CCCACCTGGATCAGCGTCGGTGGC |
| lipL (Rv1497) | F: CCCGTGACCAGCTCCCGCGACAAG<br>R: GCGGAGCGCTGGCGGTGTATCTCG |
| lipM (Rv2284) | F: TGGGTGACCGGTGAGGCGTCGAGG<br>R: AGTGCGGGCGGTCTCCTGGCTGGT |
| lipN (Rv2970c) | F: GCATGTGGACACGGCGTGTGCAGG<br>R: AACCGGCACAGCGCGTCATGGGTG |
| lipO (Rv1426c) | F: ACGCCTGGACCGGTGCTCGAAGCG<br>R: GGATCAGGGAGTCGTGGCGGCCGT |
| lipP (Rv2463) | F: GGACCAGCTCCATGTGCTCGCGGC<br>R: GGGCTCGTGCGCGTCGGAGTTCAC |
| lipQ (Rv2485c) | F: CCGGCGAACAGTCAGAGGCTGCCC<br>R: GGGCGTTGGGGAGCTCAGCGTAGG |
| lipR (Rv3084) | F: CCACTGTTGGCTTCCCGCCGGCTG<br>R: TCGTCGCCCGCGGTCTGCATGACG |
| lipS (Rv3176c) | F: CGCACCGGGCGAGCGCGCTCATCAG<br>R: CCTCGGCGAGCCGATCGGGGTGCTC |
| lipT (Rv2045c) | F: ACGGCCACCGGCATCGTTGAAGGC<br>R: CGCTGGGTTTCCGAGATCGCCCTGG |
| lipU (Rv1076) | F: GTGTTGCCGGCGGACGGCACTCGA<br>R: GACGCAACGAGCGGATCGCCTCGG |
| lipV (Rv3203) | F: CCCATCGCCGCACCCGATCTGCTGG<br>R: GCGCGGTCCCAGTCGACTGCGGATC |
| lipW (Rv0217c) | F: ATCGGCGTCGTCACCCCACGACAG<br>R: CCGCATCGCCAAGATATGCCCGCC |
| lipX (Rv1169c) | F: TTTGTCACCACACGGCCCGATTCG<br>R: GCGCGGTTGGCTAATTCGGTGAGC |

TABLE 1-continued

Primers used for RT-PCR analyses of transcripts of lipase genes induced in *M. tuberculosis* (SEQ ID NOS 3-50 respectively in order of appearance)

| Gene | Primer pairs (5'-3') |
|---|---|
| lipY (Rv3097c) | F: AGCCGCTGCCGAGGACGAGGTGTC<br>R: GGTCCCGGGAGTGCCTCCTTCCTG |
| lipZ (Rv1834) | F: CCGAGTGTCCGGGAGTGGCGTGAC<br>R: AGCCTCGACCTGCGGGTAGTGGCC |

F: Forward, R: Reverse

*Mycobacterium tuberculosis* triacylglycerol hydrolase

TABLE 2

PCR primers used for lipY disruption in *M. tuberculosis* H37Rv

| | | |
|---|---|---|
| Primer pairs to amplify 5' and 3'-flanks of lipY (SEQ ID NOS 51-54) | | |
| 5'-flank | A | 5'-GCTTAAGATGCCGTAGGACCCG-3' |
| | B | 5'-GGTCTAGAGACATCACCTCCGGC-3' |
| 3-flank | C | 5'-GGAAGCTTACTCGGTATCGCCGC-3' |
| | D | 5'-GGACTAGTGGTGCAAAGTCCGGG-3' |
| Primer pair from the deleted segment (SEQ ID NOS 55-56) | | |
| | Δ-F | 5'-GTGCAGGCATTGACAGGCGCGGCC-3' |
| | Δ-R | 5'-CCAGGTCCCCACATCGAGCCACGG-3' |
| Primer pairs to amplify genomic flanks in the mutants (SEQ ID NOS 57-60) | | |
| 5'-flank | E | 5'-GTGACCGGGAGATCCGAGCAGAGG-3' |
| | H1 | 5'-TGAGGCGATGGTGGTGTCGATGCT-3' |
| 3'-flank | H2 | 5'-GGAACTGGCGCAGTTCCTCTGGGG-3' |
| | F | 5'-CCAAGGGCTGGGGTGCACAACTCC-3' |

*Mycobacterium tuberculosis* triacylglycerol hydrolase

TABLE 3

Long-Chain TG Hydrolase activity of expressed lzp genes

| Gene Product | TG hydrolase activity (nmol/mg/min) |
|---|---|
| LIPY | 48.6 |
| LIPK | 5.6 |
| LIPL | 3.4 |
| LIPC | 3.3 |
| LIPX | 0.6 |
| LIPG | 0.4 |
| LIPE | 0.14 |
| LIPQ | 0.11 |
| LIPR | 0.11 |

TABLE 3-continued

| Long-Chain TG Hydrolase activity of expressed lzp genes | |
|---|---|
| Gene Product | TG hydrolase activity (nmol/mg/min) |
| LIPP | 0.06 |
| LIPT | 0.06 |
| LIPW | 0.05 |
| LIPD | 0.05 |
| LIPJ | 0.04 |
| LIPZ | 0.03 |
| LIPS | 0.03 |
| LIPM | 0.02 |
| LIPO | 0.005 |
| LIPF | 0 |
| LIPH | 0 |
| LIPI | 0 |
| LIPN | 0 |
| LIPU | 0 |
| LIPV | 0 |

Lipase genes were expressed in *E. coli* BL21 cells and lysates were assayed for TG hydrolase activity with $^{14}$C-labeled triolein as the substrate.

*Mycobacterium tuberculosis* triacylglycerol hydrolase

TABLE 4

| Effect of salts on LIPY activity | | |
|---|---|---|
| Effector | Concentration | Activity (nmol/mg/min) Mean ± SD |
| None | — | 643.3 ± 65.0 |
| NaCl | 200 mM | 681.3 ± 87.2 |
| KCl | 50 mM | 675.2 ± 103.5 |
| | 100 mM | 686.8 ± 68.8 |
| $MgCl_2$ | 50 mM | 306.3 ± 111.1 |
| | 100 mM | 219.9 ± 34.3 |
| $ZnCl_2$ | 10 mM | 358.7 ± 4.2 |
| | 50 mM | 5.1 ± 2.5 |
| $MnCl_2$ | 50 mM | 354.3 ± 136.5 |
| | 100 mM | 93.8 ± 7.8 |
| $CoCl_2$ | 10 mM | 424.8 ± 21.2 |
| | 50 mM | 22.9 ± 9.9 |
| $CaCl_2$ | 50 mM | 405.1 ± — |
| | 100 mM | 433.8 ± — |
| | 200 mM | 103.7 ± 29.8 |
| $CH_3COO.K$ | 50 mM | 692.6 ± 57.0 |
| | 100 mM | 749.0 ± 73.3 |

TABLE 4-continued

| Effect of salts on LIPY activity | | |
|---|---|---|
| Effector | Concentration | Activity (nmol/mg/min) Mean ± SD |
| $CH_3COO.Na$ | 50 mM | 681.7 ± 80.3 |
| | 100 mM | 729.3 ± 96.5 |

Purified LIPY protein was incubated for 15 min at room temperature with indicated concentrations of salts and then assayed radiometrically for triolein hydrolase activity as described in Experimental Procedures.

*Mycobacterium tuberculosis* triacylglycerol hydrolase

TABLE 5

| Lipase/Esterase-like Proteins in *M. tuberculosis* | | | | | |
|---|---|---|---|---|---|
| | | | Theoretical | | Conserved |
| Gene Product | | Identity (%) | MW kDa | pI | Active-site Residues |
| LIPY* | (Rv3097c) | 100.0 | 45.0 | 4.5 | GDSAG (SEQ ID NO: 61) |
| LIPP | (Rv2463) | 21.4 | 42.8 | 6.0 | |
| LIPM | (Rv2284) | 21.0 | 46.7 | 9.6 | |
| LIPL | (Rv1497) | 19.5 | 45.8 | 9.3 | |
| LIPD | (Rv1923) | 19.0 | 47.2 | 6.7 | |
| LIPH | (Rv1399c) | 18.9 | 33.9 | 4.3 | GWSLG (SEQ ID NO: 62) |
| LIPE | (Rv3775) | 18.8 | 45.3 | 8.6 | |
| LIPU | (Rv1076) | 18.5 | 31.7 | 6.3 | GDSAG (SEQ ID NO: 61) |
| LIPW | (Rv0217c) | 18.4 | 32.2 | 8.3 | GASAG (SEQ ID NO: 63) |
| LIPO | (Rv1426c) | 18.3 | 46.1 | 10.5 | |
| LIPI | (Rv1400c) | 18.2 | 34.0 | 4.6 | GDSAG (SEQ ID NO: 61) |
| LIPQ | (Rv2485c) | 18.2 | 45.2 | 8.9 | |
| LIPN | (Rv2970c) | 18.1 | 40.1 | 6.4 | GDSAG (SEQ ID NO: 61) |
| LIPG | (Rv0646c) | 17.9 | 32.9 | 9.9 | GASMG (SEQ ID NO: 64) |
| LIPK | (Rv2385) | 17.9 | 32.9 | 8.1 | |
| LIPF | (Rv3487c) | 17.8 | 29.4 | 7.7 | GDSAG (SEQ ID NO: 61) |
| LIPT | (Rv2045c) | 17.6 | 56.1 | 8.7 | GESAG (SEQ ID NO: 65) |

TABLE 5-continued

Lipase/Esterase-like Proteins in *M. tuberculosis*

| Gene Product | Identity (%) | Theoretical MW kDa | Theoretical pI | Conserved Active-site Residues |
|---|---|---|---|---|
| LIPZ* (Rv1834) | 17.4 | 31.6 | 9.4 | |
| LIPR (Rv3084) | 17.1 | 32.6 | 9.9 | GDSAG (SEQ ID NO: 61) |
| LIPC (Rv0220) | 16.7 | 44.3 | 10.4 | GCSAG (SEQ ID NO: 66) |
| LIPJ (Rv1900c) | 16.4 | 49.7 | 5.4 | |
| LIPV (Rv3203) | 15.8 | 23.6 | 4.5 | GHSFG (SEQ ID NO: 67) |
| LIPS (Rv3176c) | 15.2 | 35.2 | 6.4 | |
| LIPX* (Rv1169c) | 8.71 | 0.8 | 5.9 | |

Amino acid identity of lipase genes were compared by pairwise alignment with LIPY, which had the highest TG hydrolase activity, using the ALIGN software program at Genestream (http://www2.igh.cnrs.fr/bin/align-guess.cgi). *, We identified these genes as putative lipases as described in Experimental Procedures.

What is claimed is:

1. A method of screening for agents that modulate *Mycobacterium tuberculosis* triacylglycerol hydrolase (MTTGH) comprising the steps of i) contacting a test compound with a *Mycobacterium tuberculosis* triacylglycerol hydrolase (MTTGH) polypeptide, and ii) detecting binding of said test compound to said MTTGH polypeptide, wherein a test compound which binds to said MTTGH polypeptide is identified as an agent for modulating the activity of *Mycobacterium tuberculosis* triacylglycerol hydrolase.

2. A method of screening for agents that modulate *Mycobacterium tuberculosis* triacylglycerol hydrolase (MTTGH) comprising the steps of i) determining the activity of a MTTGH polypeptide in the presence or in the absence of a test compound, and ii) identifying a test compound that modulates the activity of a MTTGH polypeptide as a potential agent for modulating the activity of *Mycobacterium tuberculosis* triacylglycerol hydrolase.

3. A method of screening for agents that modulate *Mycobacterium tuberculosis* triacylglycerol hydrolase (MTTGH) comprising the steps of i) determining the activity of a MTTGH polypeptide in the presence of a test compound, ii) determining the activity of a MTTGH polypeptide in the presence of a compound known to be a regulator of a MTTGH polypeptide and (iii) comparing activity of step (i) with step (ii), wherein a test compound that modulates the activity of MTTGH polypeptide is identified as an agent for modulating the activity of *Mycobacterium tuberculosis* triacylglycerol hydrolase.

4. The method of claim 1, further comprising the step of obtaining a cell which has been engineered to express a MTTGH polypeptide and wherein the step of contacting is in or at the surface of said cell.

5. The method of claim 4, wherein the cell is in vitro.

6. The method of claim 1, wherein the step of contacting is in a cell-free system.

7. The method of claim 1, wherein the polypeptide is coupled to a detectable label.

8. The method of claim 1, wherein the compound is coupled to a detectable label.

9. The method of claim 1, wherein said MTTGH polypeptide comprises a ligand bound thereto and the test compound displaces said ligand.

10. The method of claim 1, wherein the polypeptide is aft ached to a solid support.

11. The method of claim 1, wherein the compound is attached to a solid support.

12. A method of screening for agents that modulate *Mycobacterium tuberculosis* triacylglycerol hydrolase (MTTGH) comprising the steps of i) contacting a test compound with a MTTGH polynucleotide, ii) detecting binding of said test compound to said MTTGH polynucleotide, wherein a test compound that binds to said MTTGH polynucleotide is identified as a potential agent for modulating the activity of *Mycobacterium tuberculosis* triacylglycerol hydrolase.

13. The method of claim 12 wherein the nucleic acid molecule is RNA.

14. The method of claim 12, further comprising the step of obtaining a cell which has been engineered to express a MTTGH polypeptide wherein the contacting step is in or at the surface of said cell.

15. The method of claim 12 wherein the contacting step is in a cell-free system.

16. The method of claim 12 wherein polynucleotide is coupled to a detectable label.

17. The method of claim 12 wherein the test compound is coupled to a detectable label.

18. A recombinant cell host containing a purified MTTGH polynucleotide or a recombinant vector comprising a MTTGH polynucleotide, wherein said MTTGH polynucleotide is SEQ. ID No. 1, or a sequence having at least 90 percent identity therewith.

* * * * *

SEQUENCE LISTING

<160> NUMBER OF SEQ ID NOS: 79

<210> SEQ ID NO 1
<211> LENGTH: 1315
<212> TYPE: DNA
<213> ORGANISM: Mycobacterium tuberculosis

<400> SEQUENCE: 1

```
gtggtgtctt atgttgttgc gttgccggag gtgatgtccg ccgcggccac agacgtggct     60

tcgattggtt cggtggtcgc gacggcgagc cagggtgtcg cgggtgccac cacgacggta    120

ttagccgctg ccgaggacga ggtgtcagcc gcgatcgcgg ctttgttttc cggccatggt    180

caggactatc aagctcttag cgcacagctt gcggtgtttc atgagcggtt tgtgcaggca    240

ttgacaggcg cggccaaggg gtatgccgcc gccgagctgg ccaacgcttc gctgttgcag    300

agtgaattcg ccagcggtat cgggaacggt tttgccacga ttcaccagga aattcagcgg    360

gcccccacgg cgctggccgc cggattcacg caggttccgc ctttcgcggc ggcgcaggca    420

gggatcttca ccggcacgcc gtcaggggct gccggattcg acatcgcttc gctgtggccg    480

gtgaaacccc tgctgagttt gtctgcgctc gaaactcact ttgcaatccc aaacaatcca    540

cttttagcgc tcattgccag cgacataccg ccgctgtcgt ggtttcttgg caactcccca    600

ccgccgttgc tgaactcgct gctgggacag acggtccagt acaccaccta tgacgggatg    660

agcgtcgtgc agatcacgcc ggctcatcca accggcgaat acgtggttgc cattcacggc    720

ggcgcgttta tcctgccgcc gtcaatcttc cactggctca actactcggt gacggcttac    780

cagaccggcg cgaccgtgca agtgccgatt tacccgttgg tgcaggaagg aggcactgcc    840

gggacggtag taccggcgat ggccgggctc atctccacgc aaatcgcgca acacggggtc    900

tccaacgtca gcgtggtcgg ggactccgcg ggcggcaacc tcgcactggc ggccgcccaa    960

tacatggtga gccagggcaa cccagtaccg tcgtccatgg tgttgctgtc cccgtggctc   1020
```

-continued

```
gatgtgggga cctggcagat cagccaggcg tgggcaggca atcttgcggt caacgacccg   1080

ctggtcagtc cgctgtatgg gtcgctgaac ggtcttccgc cgacgtatgt ctattcgggc   1140

tcgcttgatc cgctcgcaca acaagcggtt gtcctcgagc acacagccgt agtccaagga   1200

gcgccgttca gcttcgtact ggccccctgg caaatccacg actggatact gctcaccccc   1260

tggggtttgc tgtcctggcc gcagattaac cagcaactcg gtatcgccgc ctgat        1315
```

<210> SEQ ID NO 2
<211> LENGTH: 437
<212> TYPE: PRT
<213> ORGANISM: Mycobacterium tuberculosis

<400> SEQUENCE: 2

```
Met Val Ser Tyr Val Val Ala Leu Pro Glu Val Met Ser Ala Ala Ala
  1               5                  10                  15

Thr Asp Val Ala Ser Ile Gly Ser Val Val Ala Thr Ala Ser Gln Gly
             20                  25                  30

Val Ala Gly Ala Thr Thr Thr Val Leu Ala Ala Ala Glu Asp Glu Val
         35                  40                  45

Ser Ala Ala Ile Ala Ala Leu Phe Ser Gly His Gly Gln Asp Tyr Gln
     50                  55                  60

Ala Leu Ser Ala Gln Leu Ala Val Phe His Glu Arg Phe Val Gln Ala
 65                  70                  75                  80

Leu Thr Gly Ala Ala Lys Gly Tyr Ala Ala Ala Glu Leu Ala Asn Ala
                 85                  90                  95

Ser Leu Leu Gln Ser Glu Phe Ala Ser Gly Ile Gly Asn Gly Phe Ala
            100                 105                 110

Thr Ile His Gln Glu Ile Gln Arg Ala Pro Thr Ala Leu Ala Ala Gly
        115                 120                 125

Phe Thr Gln Val Pro Pro Phe Ala Ala Ala Gln Ala Gly Ile Phe Thr
    130                 135                 140

Gly Thr Pro Ser Gly Ala Ala Gly Phe Asp Ile Ala Ser Leu Trp Pro
145                 150                 155                 160

Val Lys Pro Leu Leu Ser Leu Ser Ala Leu Glu Thr His Phe Ala Ile
                165                 170                 175

Pro Asn Asn Pro Leu Leu Ala Leu Ile Ala Ser Asp Ile Pro Pro Leu
            180                 185                 190

Ser Trp Phe Leu Gly Asn Ser Pro Pro Pro Leu Leu Asn Ser Leu Leu
        195                 200                 205

Gly Gln Thr Val Gln Tyr Thr Thr Tyr Asp Gly Met Ser Val Val Gln
    210                 215                 220

Ile Thr Pro Ala His Pro Thr Gly Glu Tyr Val Val Ala Ile His Gly
225                 230                 235                 240

Gly Ala Phe Ile Leu Pro Pro Ser Ile Phe His Trp Leu Asn Tyr Ser
                245                 250                 255

Val Thr Ala Tyr Gln Thr Gly Ala Thr Val Gln Val Pro Ile Tyr Pro
            260                 265                 270

Leu Val Gln Glu Gly Gly Thr Ala Gly Thr Val Val Pro Ala Met Ala
        275                 280                 285

Gly Leu Ile Ser Thr Gln Ile Ala Gln His Gly Val Ser Asn Val Ser
    290                 295                 300

Val Val Gly Asp Ser Ala Gly Gly Asn Leu Ala Leu Ala Ala Ala Gln
305                 310                 315                 320
```

-continued

```
Tyr Met Val Ser Gln Gly Asn Pro Val Pro Ser Ser Met Val Leu Leu
                325                 330                 335

Ser Pro Trp Leu Asp Val Gly Thr Trp Gln Ile Ser Gln Ala Trp Ala
            340                 345                 350

Gly Asn Leu Ala Val Asn Asp Pro Leu Val Ser Pro Leu Tyr Gly Ser
        355                 360                 365

Leu Asn Gly Leu Pro Pro Thr Tyr Val Tyr Ser Gly Ser Leu Asp Pro
    370                 375                 380

Leu Ala Gln Gln Ala Val Val Leu Glu His Thr Ala Val Val Gln Gly
385                 390                 395                 400

Ala Pro Phe Ser Phe Val Leu Ala Pro Trp Gln Ile His Asp Trp Ile
                405                 410                 415

Leu Leu Thr Pro Trp Gly Leu Leu Ser Trp Pro Gln Ile Asn Gln Gln
            420                 425                 430

Leu Gly Ile Ala Ala
        435
```

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ggtaagcacc tcaagccgct cggc 24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gcgctgaacc actacccgct ccag 24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
ggtgttcagc gggcgagcga gttc 24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
ggcgcaacca ccgtcactcc tcac 24

<210> SEQ ID NO 7
<211> LENGTH: 24
<212> TYPE: DNA
<213> ORGANISM: Artificial Sequence -continued
<220> FEATURE:
<223> OTHER INFORMATION: Description of Artificial Sequence: Synthetic
primer

<400> SEQUENCE: 7
ctagacgccg tcacggcaac cggc 24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
actgggcgcg accagcggca catc 24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
cgacggcgct gggcgggtgg tgct 24

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
cgcgccacgg cttgcggcgc gaggt 25

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11
ctgatcatgg gcctgggcgc ccag 24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
ggacccgtga gcagcgccag cagc 24

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gaccttcacc gcggccgacg gtgtc 25

-continued

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgcgtgcaac gccctcttca gcgcc 25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggatcgagg ccgtgcgcca gcggt 25

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcacaacccg tagcgccacc agccc 25

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
cgcacggtcg aggacaccag cacc 24

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
acccggtagg cgcccaggtt cgtc 24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccagacggg ccgtggggga tatg 24

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer -continued

<400> SEQUENCE: 20
cccacctgga tcagcgtcgg tggc 24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
cccgtgacca gctcccgcga caag 24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gcggagcgct ggcggtgtat ctcg 24

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
tgggtgaccg gtgaggcgtc gagg 24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
agtgcgggcg gtctcctggc tggt 24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
gcatgtggac acggcgtgtg cagg 24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
aaccggcaca gcgcgtcatg ggtg 24

-continued

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 27
acccctggac cggtgctcga agcg 24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 28
ggatcaggga gtcgtggcgg ccgt 24

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 29
ggaccagctc catgtgctcg cggc 24

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 30
gggctcgtgc gcgtcggagt tcac 24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ccggcgaaca gtcagaggct gccc 24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 32
gggcgttggg gagctcagcg tagg 24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 33
ccactgttcg cttcccgccg gctg 24

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34
tcgtcgcccg cggtctgcat gacg 24

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35
cgcaccgggc gagcgcgctc atcag 25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36
cctcggcgag ccgatcgggc tgctc 25

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37
acggccaccg gcatcgttga aggc 24

<210> SEQ ID NO 38
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38
cgctgggctt tccgagatcg ccctgg 26

<210> SEQ ID NO 39
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 39
gtgttgccgg cggacggcac tcga 24

-continued

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 40
gacgcaacga gcggatcgcc tcgg 24

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 41
cccatcgccg cacccgatct gctgg 25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 42
gcgcggtccc agtcgactgc ggatc 25

<210> SEQ ID NO 43
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
atcgccgtcg tcaccccacg acag 24

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
ccgcatcgcc aagatatgcc cgcc 24

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
tttgtcacca cacggcccga ttcg 24

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
primer -continued

<400> SEQUENCE: 46
gcgcggttgg ctaattcggt gagc 24

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
agccgctgcc gaggacgagg tgtc 24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cgtcccggca gtgcctcctt cctg 24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ccgagtgtcc gggagtggcg tgac 24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
agcctcgacc tgcgggtagt ggcc 24

<210> SEQ ID NO 51
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
gcttaagatg ccgtaggacc cg 22

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
ggtctagaga catcacctcc ggc 23

-continued

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
ggaagcttac tcggtatcgc cgc 23

<210> SEQ ID NO 54
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
ggactagtgg tgcaaagtcc ggg 23

<210> SEQ ID NO 55
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
gtgcaggcat tgacaggcgc ggcc 24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ccaggtcccc acatcgagcc acgg 24

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 57
gtgaccggga gatccgagca gagg 24

<210> SEQ ID NO 58
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 58
tgaggcgatg gtggtgtcga tgct 24

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 59
ggaactggcg cagttcctct gggg 24

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
ccaagggctg gggtgcacaa ctcc 24

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Asp Ser Ala Gly
1 5

<210> SEQ ID NO 62
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Gly Trp Ser Leu Gly
1 5

<210> SEQ ID NO 63
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Gly Ala Ser Ala Gly
1 5

<210> SEQ ID NO 64
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Gly Ala Ser Met Gly
1 5

<210> SEQ ID NO 65
<211> LENGTH: 5
<212> TYPE: PRT
<213> ORGANISM: Artificial Sequence
<220> FEATURE:
<223> OTHER INFORMATION: Description of Artificial Sequence: Synthetic
peptide -continued

```
<400> SEQUENCE: 65

Gly Glu Ser Ala Gly
  1               5


<210> SEQ ID NO 66
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Gly Cys Ser Ala Gly
  1               5


<210> SEQ ID NO 67
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly His Ser Phe Gly
  1               5


<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Gly Gly Gly
  1


<210> SEQ ID NO 69
<211> LENGTH: 178
<212> TYPE: PRT
<213> ORGANISM: Mycobacterium tuberculosis

<400> SEQUENCE: 69

Glu Tyr Val Val Ala Ile His Gly Gly Ala Phe Ile Leu Pro Pro Ser
  1               5                  10                  15

Ile Phe His Trp Leu Asn Tyr Ser Val Thr Ala Tyr Gln Thr Gly Ala
             20                  25                  30

Thr Val Gln Val Pro Ile Tyr Pro Leu Val Gln Glu Gly Gly Thr Ala
         35                  40                  45

Gly Thr Val Val Pro Ala Met Ala Gly Leu Ser Asn Val Ser Val Val
     50                  55                  60

Gly Asp Ser Ala Gly Gly Asn Leu Ala Leu Ala Ala Ala Gln Tyr Met
 65                  70                  75                  80

Val Ser Gln Gly Asn Pro Val Pro Ser Ser Met Val Leu Leu Ser Pro
                 85                  90                  95

Trp Leu Asp Val Gly Thr Trp Gln Ile Ser Gln Ala Trp Ala Gly Asn
            100                 105                 110

Leu Ala Val Asn Leu Pro Pro Thr Tyr Val Tyr Ser Gly Ser Leu Asp
        115                 120                 125
```

-continued

```
Pro Leu Ala Gln Gln Ala Val Val Leu Glu His Thr Ala Val Val Gln
    130                 135                 140

Gly Ala Pro Phe Ser Phe Val Leu Ala Pro Trp Gln Ile His Asp Trp
145                 150                 155                 160

Ile Leu Leu Thr Pro Trp Gly Leu Leu Ser Trp Pro Gln Ile Asn Gln
                165                 170                 175

Gln Leu


<210> SEQ ID NO 70
<211> LENGTH: 181
<212> TYPE: PRT
<213> ORGANISM: Archaeoglobus fulgidus

<400> SEQUENCE: 70

Pro Val Leu Val Tyr Tyr His Gly Gly Gly Phe Val Ile Cys Ser Ile
  1               5                  10                  15

Glu Ser His Asp Ala Leu Cys Arg Arg Ile Ala Arg Leu Ser Asn Ser
             20                  25                  30

Thr Val Val Ser Val Asp Tyr Arg Leu Ala Pro Glu His Lys Phe Pro
         35                  40                  45

Ala Ala Val Tyr Asp Cys Tyr Asp Ala Thr Ser Lys Ile Phe Val Gly
     50                  55                  60

Gly Asp Ser Ala Gly Gly Asn Leu Ala Ala Ala Val Ser Ile Met Ala
 65                  70                  75                  80

Arg Asp Ser Gly Glu Asp Phe Ile Lys His Gln Ile Leu Ile Tyr Pro
                85                  90                  95

Val Val Asn Phe Val Ala Pro Thr Pro Ser Leu Leu Glu Phe Gly Glu
            100                 105                 110

Gly Leu Trp Ile Leu Pro Pro Ala Leu Ile Ile Thr Ala Glu Tyr Asp
        115                 120                 125

Pro Leu Arg Asp Glu Gly Glu Val Phe Gly Gln Met Leu Arg Arg Ala
    130                 135                 140

Gly Val Glu Ala Ser Ile Val Arg Tyr Arg Gly Val Leu His Gly Phe
145                 150                 155                 160

Ile Asn Tyr Tyr Pro Val Leu Lys Ala Ala Arg Asp Ala Ile Asn Gln
                165                 170                 175

Ile Ala Ala Leu Leu
            180


<210> SEQ ID NO 71
<211> LENGTH: 180
<212> TYPE: PRT
<213> ORGANISM: Acinetobacter esterase

<400> SEQUENCE: 71

Pro Leu Ile Val Phe Tyr His Gly Gly Gly Phe Val Val Gly Gly Leu
  1               5                  10                  15

Asp Ser His Asp Glu Phe Cys Arg Leu Met Ala Val His Ala His Ala
             20                  25                  30

Gln Val Leu Ser Val Glu Tyr Pro Leu Ala Pro Glu Ala Ser Pro Gln
         35                  40                  45

Gln Ile Ile Gln Val Cys Glu Asp Ala Leu Asn Arg Ile Ala Val Ala
     50                  55                  60

Gly Asp Ser Ala Gly Gly Asn Ile Ala Ala Val Val Ala Gln Arg Ser
 65                  70                  75                  80
```

-continued

Ala Gln Ser Ala Tyr Ala Pro Asn Ala Gln Phe Leu Ile Tyr Pro Ala
85 90 95

Leu Asp Phe Lys Ser Arg His Pro Ser Phe Phe Ala Tyr Lys Asp Gly
100 105 110

Leu Val Leu Leu Ala Pro Ala Phe Val Val Thr Ala Gly His Asp Val
115 120 125

Leu His Asp Glu Ala Glu Ile Tyr Ala His Lys Leu Arg Gln Asn Gln
130 135 140

Val Thr Val Lys Tyr Val Glu Tyr Leu Asp Gln Thr His Gly Phe Ile
145 150 155 160

Ser Met Thr Phe Val Ser Arg Arg Ala Lys Lys Ile Ser Ile Glu Leu
165 170 175

Cys Lys Asn Phe
180

<210> SEQ ID NO 72
<211> LENGTH: 183
<212> TYPE: PRT
<213> ORGANISM: Homo sapiens

<400> SEQUENCE: 72

Ser Leu Ile Val His Phe His Gly Gly Gly Phe Val Ala Gln Thr Ser
1 5 10 15

Arg Ser His Glu Pro Tyr Leu Lys Ser Trp Ala Gln Glu Leu Gly Ala
20 25 30

Pro Ile Ile Ser Ile Asp Tyr Ser Leu Ala Pro Glu Ala Pro Phe Pro
35 40 45

Arg Ala Leu Glu Glu Cys Phe Phe Ala Tyr Glu Arg Ile Cys Leu Ala
50 55 60

Gly Asp Ser Ala Gly Gly Asn Leu Cys Phe Thr Val Ala Leu Arg Ala
65 70 75 80

Ala Ala Tyr Gly Val Arg Val Pro Asp Gly Ile Met Ala Ala Tyr Pro
85 90 95

Ala Thr Met Leu Gln Pro Ala Ala Ser Pro Ser Arg Leu Leu Ser Leu
100 105 110

Met Asp Pro Leu Leu Pro Pro Val His Ile Val Ala Cys Ala Leu Asp
115 120 125

Pro Met Leu Asp Asp Ser Val Met Leu Ala Arg Arg Leu Arg Asn Leu
130 135 140

Gly Gln Pro Val Thr Leu Arg Val Val Glu Asp Leu Pro His Gly Phe
145 150 155 160

Leu Thr Leu Ala Ala Leu Cys Arg Glu Thr Arg Gln Ala Ala Glu Leu
165 170 175

Cys Val Glu Arg Ile Arg Leu
180

<210> SEQ ID NO 73
<211> LENGTH: 183
<212> TYPE: PRT
<213> ORGANISM: Pseudomonas sp.

<400> SEQUENCE: 73

Pro Leu Leu Val Phe Phe His Gly Gly Gly Phe Val Met Gly Asn Leu
1 5 10 15

Asp Thr His Asp Asn Leu Cys Arg Ser Leu Ala Ser Gln Thr Glu Ala
20 25 30

-continued

```
Val Val Val Ser Val Ala Tyr Arg Leu Ala Pro Glu Asn His Phe Pro
        35                  40                  45

Ala Ala Pro Leu Asp Cys Tyr Ala Ala Thr Arg Arg Leu Ala Leu Ala
    50                  55                  60

Gly Asp Ser Ala Gly Gly Asn Leu Ala Leu Ala Val Ser Arg Leu Ala
65                  70                  75                  80

Ala Gln Arg Gln Gly Pro Lys Ile Ser Tyr Gln Cys Leu Phe Tyr Pro
                85                  90                  95

Val Thr Asp Ala Arg Cys Asp Ser Gln Ser Tyr Glu Glu Phe Ala Glu
            100                 105                 110

Gly Tyr Phe Leu Leu Pro Pro Thr Thr Leu Ile Thr Ala Glu Phe Asp
        115                 120                 125

Pro Leu Arg Asp Glu Gly Glu Ala Phe Ala Leu Arg Leu Gln Gln Ala
    130                 135                 140

Gly Val Ser Val Arg Val Gln Arg Cys Glu Gly Met Ile His Gly Phe
145                 150                 155                 160

Ile Ser Met Ala Pro Phe Val Glu Arg Ala Ala His Ala Leu Ser Asp
                165                 170                 175

Ala Ala Ala Asp Leu Arg Arg
            180
```

```
<210> SEQ ID NO 74
<211> LENGTH: 185
<212> TYPE: PRT
<213> ORGANISM: Bacillus subtilis

<400> SEQUENCE: 74

Pro Gly Leu Val Tyr Thr His Gly Gly Gly Met Thr Ile Leu Thr Thr
1               5                   10                  15

Asp Asn Arg Val His Arg Arg Trp Cys Thr Asp Leu Ala Ala Ala Gly
            20                  25                  30

Ser Val Val Val Met Val Asp Phe Arg Asn Ala Trp Thr Ala Glu Gly
        35                  40                  45

His His Pro Phe Pro Ser Gly Val Glu Asp Cys Leu Ser Gly Val Val
    50                  55                  60

Val Gln Gly Glu Ser Gly Gly Gly Asn Leu Ala Ile Ala Thr Thr Leu
65                  70                  75                  80

Leu Ala Lys Arg Arg Gly Arg Leu Asp Ala Ile Asp Gly Val Tyr Ala
                85                  90                  95

Ser Ile Pro Tyr Ile Ser Gly Gly Tyr Ala Trp Asp His Glu Arg Arg
            100                 105                 110

Leu Thr Glu Leu Pro Ser Leu Pro Pro Phe Val Val Ala Val Asn Glu
        115                 120                 125

Leu Asp Pro Leu Arg Asp Glu Gly Ile Ala Phe Ala Arg Arg Leu Ala
    130                 135                 140

Arg Ala Gly Val Asp Val Ala Ala Arg Val Asn Ile Gly Leu Val His
145                 150                 155                 160

Gly Ala Asp Val Ile Phe Arg His Trp Leu Pro Ala Ala Leu Glu Ser
                165                 170                 175

Thr Val Arg Asp Val Ala Gly Phe Ala
            180                 185
```

```
<210> SEQ ID NO 75
<211> LENGTH: 181
<212> TYPE: PRT
<213> ORGANISM: Mycobacterium tuberculosis
```

-continued

<400> SEQUENCE: 75

```
Arg Ala Val Leu Tyr Leu His Gly Gly Ala Phe Leu Thr Cys Gly Ala
  1               5                  10                  15

Asn Ser His Gly Arg Leu Val Glu Leu Leu Ser Lys Phe Ala Asp Ser
             20                  25                  30

Pro Val Leu Val Val Asp Tyr Arg Leu Ile Pro Lys His Ser Ile Gly
         35                  40                  45

Met Ala Leu Asp Asp Cys His Asp Gly Tyr Glu Gln Ile Val Leu Ala
     50                  55                  60

Gly Asp Ser Ala Gly Gly Tyr Leu Ala Leu Ala Leu Ala Gln Arg Leu
 65                  70                  75                  80

Gln Glu Val Gly Glu Glu Pro Ala Ala Leu Val Ala Ile Ser Pro Leu
                 85                  90                  95

Leu Gln Leu Ala Lys Glu His Lys Gln Ala His Pro Asn Ile Lys Thr
            100                 105                 110

Asp Ala Met Phe Leu Pro Arg Thr Leu Ile His Val Ser Gly Ser Glu
        115                 120                 125

Val Leu Leu His Asp Ala Gln Leu Ala Ala Ala Lys Leu Ala Ala Ala
    130                 135                 140

Gly Val Pro Ala Glu Val Arg Val Trp Pro Gly Gln Val His Asp Phe
145                 150                 155                 160

Gln Val Ala Ala Ser Met Leu Pro Glu Ala Ile Arg Ser Leu Arg Gln
                165                 170                 175

Ile Gly Glu Tyr Ile
            180
```

<210> SEQ ID NO 76
<211> LENGTH: 178
<212> TYPE: PRT
<213> ORGANISM: Mycobacterium tuberculosis

<400> SEQUENCE: 76

```
Glu Tyr Val Val Ala Ile His Gly Gly Ala Phe Ile Leu Pro Pro Ser
  1               5                  10                  15

Ile Phe His Trp Leu Asn Tyr Ser Val Thr Ala Tyr Gln Thr Gly Ala
             20                  25                  30

Thr Val Gln Val Pro Ile Tyr Pro Leu Val Gln Glu Gly Gly Thr Ala
         35                  40                  45

Gly Thr Val Val Pro Ala Met Ala Gly Leu Ser Asn Val Ser Val Val
     50                  55                  60

Gly Asp Ser Ala Gly Gly Asn Leu Ala Leu Ala Ala Ala Gln Tyr Met
 65                  70                  75                  80

Val Ser Gln Gly Asn Pro Val Pro Ser Ser Met Val Leu Leu Ser Pro
                 85                  90                  95

Trp Leu Asp Val Gly Thr Trp Gln Ile Ser Gln Ala Trp Ala Gly Asn
            100                 105                 110

Leu Ala Val Asn Leu Pro Pro Thr Tyr Val Tyr Ser Gly Ser Leu Asp
        115                 120                 125

Pro Leu Ala Gln Gln Ala Val Val Leu Glu His Thr Ala Val Val Gln
    130                 135                 140

Gly Ala Pro Phe Ser Phe Val Leu Ala Pro Trp Gln Ile His Asp Trp
145                 150                 155                 160
```

-continued

```
Ile Leu Leu Thr Pro Trp Gly Leu Leu Ser Trp Leu Gln Ile Asn Gln
                165                 170                 175

Gln Leu


<210> SEQ ID NO 77
<211> LENGTH: 181
<212> TYPE: PRT
<213> ORGANISM: Ralstonia solanacearum

<400> SEQUENCE: 77

Pro Val Val Phe Tyr Leu His Gly Gly Gly Tyr Phe Phe Cys Ser Pro
  1               5                  10                  15

Arg Thr His Arg Ser Ile Thr Ile Gly Leu Ala Val His Ala Arg Ala
             20                  25                  30

Arg Val Phe Ala Leu Asp Tyr Arg Leu Ala Pro Glu His Pro Phe Pro
         35                  40                  45

Ala Ala Val Leu Asp Ala Leu Ala Gly Tyr Ser Arg Ile Val Val Ala
     50                  55                  60

Gly Asp Ser Ala Gly Gly Gly Leu Ser Leu Ala Leu Leu Val Ala Leu
 65                  70                  75                  80

Arg Asp Ala Gly Asp Pro Leu Pro Ala Gly Ala Ile Leu Tyr Ser Pro
                 85                  90                  95

Trp Thr Asp Leu Ala Ala Thr Gly Ala Ser Leu Val Glu Asn Asp Ala
            100                 105                 110

Ser Asp Val Met Leu Pro Pro Leu His Cys Tyr Val Ser Thr Ser Glu
        115                 120                 125

Val Leu Arg Asp Asp Thr Leu Arg Met Ala Glu Arg Ala Arg Ala Ala
    130                 135                 140

Gly Val Ser Val Ser Val Glu Leu Gly Arg Arg Leu Pro His Val Trp
145                 150                 155                 160

Pro Ile Phe Tyr Pro Phe Leu Pro Glu Ala Arg Lys Ala Leu Arg Gln
                165                 170                 175

Ser Gly Asp Ala Val
            180


<210> SEQ ID NO 78
<211> LENGTH: 179
<212> TYPE: PRT
<213> ORGANISM: Staphylococcus aureus

<400> SEQUENCE: 78

Arg Val Val Leu Tyr Ala His Gly Gly Ala Trp Phe Gln Asp Pro Leu
  1               5                  10                  15

Lys Ile His Phe Glu Phe Ile Asp Glu Leu Ala Glu Thr Leu Asn Ala
             20                  25                  30

Lys Val Ile Met Pro Val Tyr Pro Lys Ile Pro His Gln Asp Tyr Gln
         35                  40                  45

Ala Thr Tyr Val Leu Phe Glu Lys Leu Tyr Lys Gln Ile Val Val Met
     50                  55                  60

Gly Asp Ser Ala Gly Gly Gln Ile Ala Leu Ser Phe Ala Gln Leu Leu
 65                  70                  75                  80

Lys Glu Lys His Ile Val Gln Pro Gly His Ile Val Leu Ile Ser Pro
                 85                  90                  95

Val Leu Asp Ala Thr Met Gln His Pro Glu Ile Pro Asp Tyr Leu Lys
            100                 105                 110
```

-continued

```
Lys Asp Pro Met Leu Gly Arg Ile Thr Leu Thr Val Gly Thr Lys Glu
        115                 120                 125

Val Leu Tyr Pro Asp Ala Leu Asn Leu Ser Gln Leu Leu Ser Ala Lys
    130                 135                 140

Gly Ile Glu His Asp Phe Ile Pro Gly Tyr Tyr Gln Phe His Ile Tyr
145                 150                 155                 160

Pro Val Phe Pro Ile Pro Glu Arg Arg Arg Phe Leu Tyr Gln Val Lys
                165                 170                 175

Asn Ile Ile


<210> SEQ ID NO 79
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 79

His His His His His His
  1               5
```